United States Patent [19]

Gilmore et al.

[11] Patent Number: 5,369,858
[45] Date of Patent: Dec. 6, 1994

[54] PROCESS FOR FORMING APERTURED NONWOVEN FABRIC PREPARED FROM MELT BLOWN MICROFIBERS

[75] Inventors: Thomas Gilmore; David Newkirk; Jared Austin, all of Greer; Guy S. Zimmerman, Jr., Greenville, all of S.C.; Milo Johnston, Doylestown, Pa.

[73] Assignee: Fiberweb North America, Inc., Simpsonville, S.C.

[21] Appl. No.: 932,378

[22] Filed: Aug. 19, 1992

Related U.S. Application Data

[62] Division of Ser. No. 386,457, Jul. 28, 1989.

[51] Int. Cl.⁵ .................. D04H 1/46; D04H 1/70; B32B 5/16
[52] U.S. Cl. .................... 28/104; 28/105; 428/284
[58] Field of Search .................. 28/104, 105; 428/284

[56] References Cited

U.S. PATENT DOCUMENTS

| | | |
|---|---|---|
| Re. 31,601 | 6/1984 | Ikeda et al. . |
| 2,862,251 | 12/1958 | Kalwaites . |
| 3,033,721 | 5/1962 | Kalwaites . |
| 3,068,547 | 12/1962 | L'Hommedieu . |
| 3,129,466 | 4/1964 | L'Hommedieu . |
| 3,214,819 | 11/1965 | Guerin . |
| 3,276,944 | 10/1966 | Levy . |
| 3,338,992 | 8/1967 | Kinney . |
| 3,341,394 | 9/1967 | Kinney . |
| 3,434,188 | 3/1969 | Summers . |
| 3,485,706 | 12/1969 | Evans . |
| 3,493,462 | 2/1970 | Bunting, Jr. et al. . |
| 3,494,821 | 2/1970 | Evans . |
| 3,498,874 | 3/1970 | Evans et al. . |
| 3,502,538 | 3/1970 | Petersen . |
| 3,502,763 | 3/1970 | Hartmann . |
| 3,508,308 | 4/1970 | Bunting, Jr. et al. . |
| 3,509,009 | 4/1970 | Hartmann . |
| 3,542,615 | 11/1970 | Dobo et al. . |
| 3,563,241 | 2/1971 | Evans et al. . |
| 3,595,245 | 7/1971 | Buntin et al. . |
| 3,620,903 | 11/1971 | Bunting, Jr. et al. . |
| 3,676,242 | 7/1972 | Prentice . |
| 3,683,921 | 8/1972 | Brooks et al. . |
| 3,692,618 | 9/1972 | Dorschner et al. . |
| 3,704,198 | 11/1972 | Prentice . |
| 3,715,251 | 2/1973 | Prentice . |
| 3,769,659 | 11/1973 | Kalwaites . |
| 3,787,932 | 1/1974 | Kalwaites . |
| 3,800,364 | 4/1974 | Kalwaites . |
| 3,815,602 | 6/1974 | Johns et al. . |
| 3,837,046 | 9/1974 | Kalwaites . |
| 3,855,046 | 12/1974 | Hansen et al. . |
| 4,041,203 | 8/1977 | Brock et al. . |
| 4,152,480 | 5/1979 | Adachi et al. . |
| 4,166,877 | 9/1979 | Brandon et al. . |
| 4,190,695 | 2/1980 | Niederhauser . |
| 4,251,581 | 2/1981 | Schoppa et al. . |
| 4,297,404 | 10/1981 | Nguyen . |
| 4,302,495 | 11/1981 | Marra . |
| 4,334,340 | 6/1982 | Reba . |
| 4,405,297 | 9/1983 | Appel . |
| 4,410,579 | 10/1983 | Johns . |

(List continued on next page.)

FOREIGN PATENT DOCUMENTS

| | | |
|---|---|---|
| 803714 | 1/1969 | Canada . |
| 841938 | 5/1970 | Canada . |

(List continued on next page.)

OTHER PUBLICATIONS

"Du Pont Unveils Spunlaced Aramid Fibers for Wide-Ranging Industrial Applications", Nonwovens Market, vol. 2, No. 23, pp. 4–5.

(List continued on next page.)

Primary Examiner—Clifford D. Crowder
Assistant Examiner—John J. Calvert
Attorney, Agent, or Firm—Bell, Seltzer, Park & Gibson

[57] ABSTRACT

A nonwoven fabric comprising at least one layer of textile fibers or net of polymeric filaments and at least one web of melt blown microfibers, bonded together by hydroentangling. The nonwoven fabric may be apertured by hydroentangling or may have areas of higher density and areas of lower density. The fabric has a favorable combination of softness, dryness, tensile strength and hand. Several processes are provided for producing the nonwoven fabric of the invention.

26 Claims, 14 Drawing Sheets

U.S. PATENT DOCUMENTS

| | | |
|---|---|---|
| 4,426,420 | 1/1984 | Likhyani . |
| 4,426,421 | 1/1984 | Nakamae et al. . |
| 4,442,161 | 4/1984 | Kirayoglu et al. . |
| 4,476,186 | 10/1984 | Kato et al. . |
| 4,514,455 | 4/1985 | Hwang . |
| 4,532,173 | 7/1985 | Suzuki et al. . |
| 4,537,819 | 8/1985 | Schortmann et al. . |
| 4,548,628 | 10/1985 | Miyake et al. . |
| 4,585,449 | 4/1986 | Karami . |
| 4,591,513 | 5/1986 | Suzuki et al. . |
| 4,636,419 | 1/1987 | Madsen et al. . |
| 4,637,819 | 1/1987 | Ouellette et al. . |
| 4,681,801 | 7/1987 | Eian et al. . |
| 4,704,112 | 11/1987 | Suzuki et al. . |
| 4,753,834 | 6/1988 | Braun et al. . |
| 4,775,579 | 10/1988 | Hagy et al. ............ 28/104 X |
| 4,808,467 | 2/1989 | Suskind et al. ............ 28/104 X |
| 4,812,112 | 3/1989 | Balk . |
| 4,818,594 | 4/1989 | Albien et al. . |
| 4,879,170 | 11/1989 | Radwanski et al. ............ 28/104 X |
| 4,902,564 | 2/1990 | Israel et al. ............ 28/104 X |
| 4,931,355 | 6/1990 | Radwanski et al. ............ 28/104 X |
| 4,939,016 | 7/1990 | Radwanski et al. ............ 28/104 X |
| 4,950,531 | 8/1990 | Radwanski et al. ............ 428/284 |

FOREIGN PATENT DOCUMENTS

| | | |
|---|---|---|
| 1123589 | 5/1982 | Canada . |
| 120564 | 10/1984 | European Pat. Off. . |
| 127851 | 12/1984 | European Pat. Off. . |
| 128667 | 12/1984 | European Pat. Off. . |
| 214608 | 3/1987 | European Pat. Off. . |
| 333209 | 9/1989 | European Pat. Off. . |
| 333210 | 9/1989 | European Pat. Off. . |
| 333211 | 9/1989 | European Pat. Off. . |
| 333228 | 9/1989 | European Pat. Off. . |
| 0343331 | 11/1989 | European Pat. Off. ............ 28/104 |
| 1217892 | 12/1970 | United Kingdom . |
| 1367944 | 9/1974 | United Kingdom ............ 28/105 |
| 1544165 | 4/1979 | United Kingdom . |
| 1550955 | 8/1979 | United Kingdom . |
| 1596718 | 8/1981 | United Kingdom . |
| 2085493 | 4/1982 | United Kingdom . |
| 2114054 | 8/1983 | United Kingdom . |
| 2114173 | 8/1983 | United Kingdom . |

OTHER PUBLICATIONS

"The Outlook for Durable and Disposable Nonwoven Markets Through the 1980's", T. M. Holliday & Assocs. and R. G. Mansfield & Assocs., pp. 167–200.

"Spunlaced Products: Technology and End–Use Applications", E. I. duPont de Nemours & Company, Inc.

"Burlington Tries Polyester/Cotton Spunlace", Nonwovens World, May–Jun. 1987, pp. 19–21.

"First Weaving, Then Knitting, Now Spunlaced Nonwovens", Nonwovens Industry, Jul. 1987, pp. 32, 34–35.

"Water Jet Entangled Nonwovens", John R. Starr, Insight 87, Sep. 21, 1987, pp. 1–20.

"Inda Looks Into the Future of Nonwovens Fabrics", INDA-TEC Nonwovens Technology Conference, Jun. 2–5, 1986, p. 5.

"Suominen Offers Wide Range of Spunlaced Nonwovens", European Disposables and Nonwovens Assoc., Newsletter Nov./Dec. 1986, vol. 12, No. 6.

"The Perfoject Entanglement Process", Andre Vuillaume, Nonwovens World, Feb. 1987, pp. 81–84.

"Progress with Sontara and Spunlaced Fabrics in Europe", Nonwovens Report, Jan. 1987, pp. 7–8.

"Composite of Synthetic-Fiber Web and Paper", Research Disclosure No. 09196/78, Jun. 1978.

"New Applications for Spunlaced Technology", H. H. Forsten Chemiefasern/Textilin dustrie, Mar. 1985, pp. 23–24.

Christian B. Widen, "Forming Wires for Hydroentanglement Systems", Nonwovens Technology, Nov. 1988, pp. 39–43.

FIG. I.

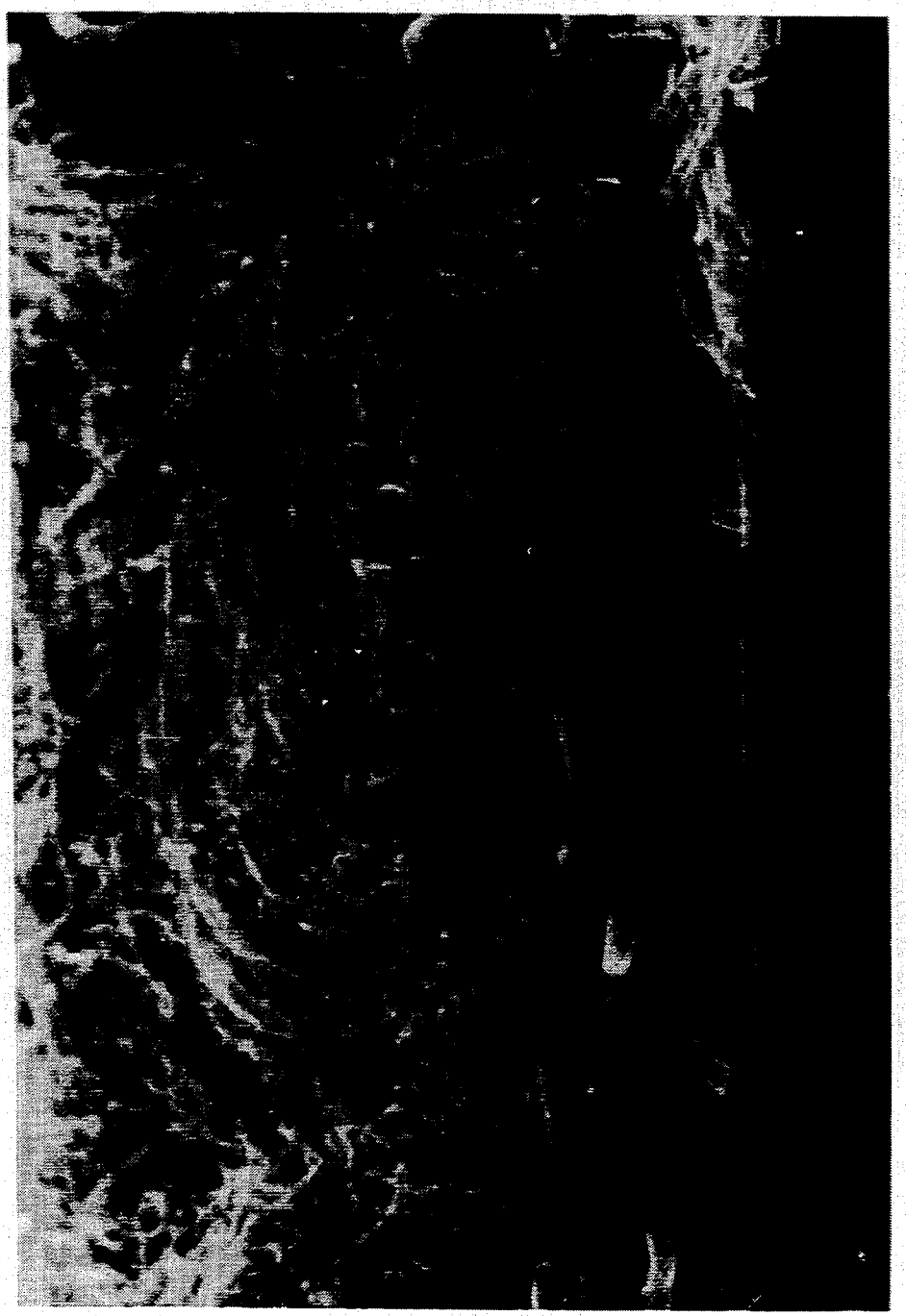

PROCESS FOR FORMING APERTURED NONWOVEN FABRIC PREPARED FROM MELT BLOWN MICROFIBERS

This application is a divisional of application Ser. No. 07/386,457, filed Jul. 28, 1989.

BACKGROUND OF THE INVENTION

The present invention relates to a nonwoven fabric for use as a fluid transmitting topsheet for disposable diapers and sanitary napkins.

Disposable diapers, sanitary napkins and the like are generally composed of an impermeable outer covering, an absorbent core and an inner layer that is commonly referred to as a topsheet, coverstock, or in diaper applications, a diaper liner. Desirable characteristics of topsheets for such absorptive articles include rapid permeability or strike-through; a dry feeling adjacent the wearer's skin, i.e., low re-transmission of liquid from the absorbent core to the body or wearer side of the topsheet (low rewet); a soft comfortable feeling to the wearer; adequate strength; the appearance of being absorptive and a clean non-stained appearance. The subjective feel, i.e., softness and dryness, of diaper liners has become more important with the increased use of diapers by incontinent adults.

Various approaches have been attempted by the prior art to obtain a fabric having the desired characteristics for use as a diaper or sanitary napkin topsheet.

One approach was to utilize a nonwoven fabric composed of hydrophilic fibers. Although such a fabric achieved a high initial permeability, this approach suffered from the disadvantage that body fluid tended to rewet the hydrophilic fabric and thus the surface in contact with the wearer's skin stayed uncomfortably wet.

Another effort attempted to utilize an upper layer of hydrophobic fibers and a lower layer of hydrophic fibers. The disadvantage of such a fabric was the difficulty in forming the layer adjacent the skin thin enough to maintain adequate permeability yet thick enough to prevent a wet feeling to the wearer.

Another approach consisted of a nonwoven fabric comprising hydrophobic fibers containing a hydrophilic agent thereon. This fabric suffered from the disadvantage that the hydrophilic agent tends to be washed away as body fluid permeates the nonwoven fabric initially and thus it becomes difficult for body fluid to repeatedly permeate the fabric.

Another attempt has been to utilize a soft thermoplastic film having a plurality of apertures, bonded to a fibrous layer. This approach suffered from the disadvantage of low breathability and permeability for moisture generated on the wearer's skin and therefore tended to create a musty condition adjacent the wearer's skin. In addition, such a fabric suffers from a lack of softness and is not comfortable next to the wearer's skin.

Another approach has been to utilize two layers of nonwoven fabric, the first layer being in contact with the wearer's skin and comprising predominantly hydrophobic fibers with a pattern of apertures therein and a second layer bonded to the first layer composed of predominantly hydrophilic fibers with no apertures. Such a nonwoven fabric suffers from a lack of softness and thus is not comfortable to the wearer.

It is an object of the present invention to provide a nonwoven fabric for use as a diaper or sanitary napkin topsheet which overcomes the problems of the prior art.

It is another object of the present invention to provide a nonwoven fabric for use as a diaper or sanitary napkin topsheet which has a high permeability.

It is another object of the present invention to provide a nonwoven fabric for use as a diaper or sanitary napkin topsheet which has low rewet properties.

It is another object of the present invention to provide a nonwoven fabric for use as a diaper or sanitary napkin topsheet which has a high softness and thus provides a comfortable feeling to the wearer.

It is another object of the present invention to provide a nonwoven fabric for use as a diaper or sanitary napkin topsheet which has adequate tensile strength and a cloth-like hand.

It is another object of the present invention to provide a nonwoven fabric for use as a diaper or sanitary napkin topsheet which has the appearance of being apertured.

It is a further object of the present invention to provide a nonwoven fabric for use as a diaper or sanitary napkin topsheet which is opaque in portions of its surface and thus provides a clean and nonstained appearance when utilized as a topsheet for diapers or sanitary napkins.

Additional objects and advantages of the invention will be set forth in part in the description which follows, and in part will be obvious from the description, or may be learned by practice of the invention. The objects and advantages of the invention will be realized and attained by means of the instrumentalities and combinations particularly pointed out in the appended claims.

SUMMARY OF THE INVENTION

As embodied and broadly described herein, the nonwoven composite fabric of the present invention comprises at least one layer selected from a web of textile fibers and a net of polymeric filaments and at least one web of melt blown microfibers, combined by hydroentangling. This nonwoven fabric has a favorable combination of softness, dryness, tensile strength and hand. In addition to being consolidated by hydroentangling, the nonwoven fabric of the present invention may also be apertured by the same hydroentangling process, or alternatively, may have regions of higher area density and regions of lower area density. The apertures in the nonwoven fabric of the invention may be a plurality of different sizes.

In another aspect of the invention, the nonwoven fabric may be produced by a process comprising:

supporting a first layer selected from a web of textile fibers and a net of polymeric filaments and a second layer of a web of melt blown microfibers on an aperturing member; and impinging streams of high pressure liquid onto the fiber layers for a time sufficient to entangle the fibers with one another such that the fibers interlock to form a fabric.

In another aspect of the invention, as embodied and broadly described herein, a process for producing a nonwoven fabric having apertures of two different sizes is provided comprising:

supporting a first layer selected from a web of textile fibers and a net of polymeric filaments and a second layer of a web of melt blown microfibers on a first aperturing member having aperturing means of a first size;

impinging streams of high pressure liquid onto the fiber layers for a time sufficient to entangle the fibers with one another such that the fibers interlock to form a fabric having apertures of a first size;

transferring the fabric to a second aperturing member having aperturing means of a second size; and impinging streams of high pressure liquid onto the fabric for a time sufficient to form apertures of a second size in the fabric.

In another aspect of the invention, as embodied and broadly described herein, a process for producing a nonwoven fabric made of a web of textile fibers and a web of melt blown microfibers is provided. This process comprises:

extruding a web of drawn continuous filament textile fibers or supplying a bonded web of drawn continuous filament textile fibers onto a continuous belt;

extruding a web of melt blown microfibers or supplying a bonded web of melt blown microfibers onto the web of drawn continuous filament textile fibers on the continuous belt;

transferring the webs onto an aperturing member; and impinging streams of high pressure liquid onto the fiber layers for a time sufficient to entangle the fibers with one another such that the fibers interlock to form a fabric.

In another aspect of the invention, as embodied and broadly described herein, a process for producing a nonwoven fabric made of a carded web of staple textile fibers and a web of melt blown microfibers is provided. The process includes, prior to the above-mentioned transferring and hydroentangling steps, the steps of:

carding a web of staple textile fibers or supplying a bonded carded web of staple textile fibers onto a continuous belt; and extruding a web of melt blown microfibers or supplying a bonded web of melt blown microfibers onto the web of carded staple textile fibers on the continuous belt.

In another aspect of the invention, as embodied and broadly described herein, a process for producing a nonwoven fabric made of a web of melt blown microfibers and a web of carded staple textile fibers can also be utilized with the melt blown web laid first on the continuous belt and the carded staple textile fiber web laid thereon. The process includes, prior to the transferring and hydroentangling steps, the steps of:

extruding a web of melt blown microfibers or supplying a bonded web of melt blown microfibers onto a continuous belt; and carding a web of staple textile fibers or supplying a bonded carded web of staple textile fibers onto the web of melt blown microfibers on the continuous belt.

In another aspect of the invention, as embodied and broadly described herein, a process for producing a nonwoven fabric made of a net of polymeric filaments and a web of melt blown microfibers is provided. The process includes, prior to the transferring and hydroentangling steps, the steps of:

supplying a net of polymeric filaments onto a continuous belt; and extruding a web of melt blown microfibers or supplying a bonded web of melt blown microfibers onto the net on the continuous belt.

In another aspect of the invention, as embodied and broadly described herein, a diaper is provided comprising a topsheet layer of a nonwoven fabric comprising:

at least one layer selected from a web of textile fibers and a net of polymeric filaments and at least one web of melt blown microfibers, the topsheet layer being in contact with the wearer's skin;

a layer of an absorbent material; and an impermeable outer covering.

The topsheet layer may be produced by bonding the layer of textile fibers to the layer of melt blown microfibers by hydroentangling. The topsheet layer may be either apertured by hydroentangling or may have regions of higher area density and regions of lower area density.

The accompanying drawings, which are incorporated in and constitute a part of this specification, illustrate preferred embodiments of the invention and together with the, detailed description of the preferred embodiments herein, serve to explain the principles of the invention.

BRIEF DESCRIPTION OF THE DRAWINGS

FIG. 7A provides a view of a region of higher area density of the spunbond web side of the product produced by Example 15 at 100X magnification via SEM.

FIG. 8B provides a cross-sectional view of the product produced by Example 15 at 100X magnification via SEM.

DETAILED DESCRIPTION OF THE PREFERRED EMBODIMENTS

Figure 1:
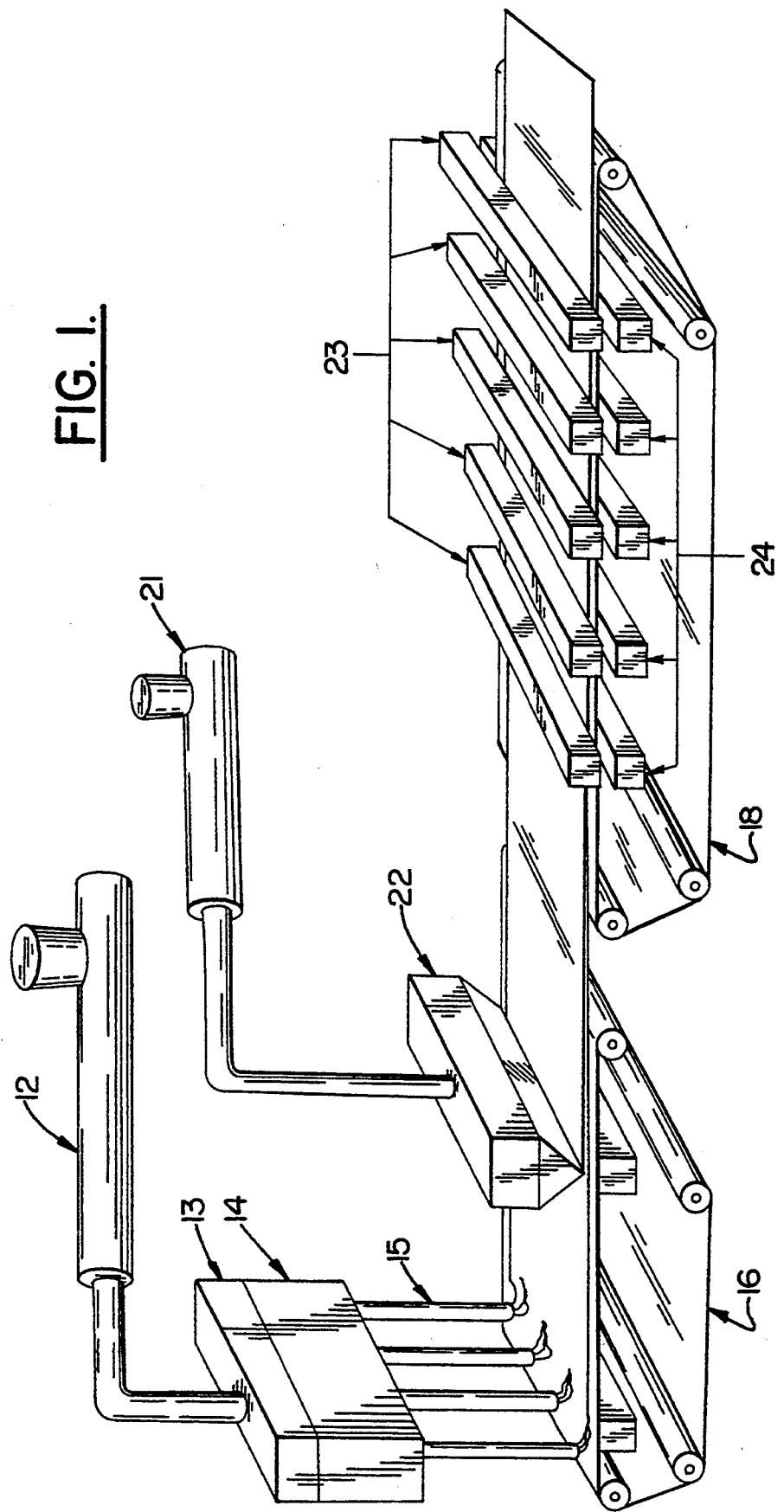
FIG. 1 is a schematic diagram illustrating a process of the present invention for producing a nonwoven fabric by directly extruding melt blown microfibers onto directly extruded drawn continuous filament textile fibers, followed by hydroentangling.

Reference will now be made in detail to the present preferred embodiments of the invention, examples of which are illustrated in the accompanying drawings and the working examples.

In accordance with the present invention, there is provided a nonwoven fabric comprising at least one layer selected from a web of textile fibers and a net of polymeric filaments and at least one web of melt blown microfibers, combined by hydroentangling. The nonwoven fabric has a favorable combination of softness, dryness, tensile strength and hand.

Textile fibers are those fibers having sufficient strength to be converted into yarn or processed into fabric by various textile methods, including weaving, knitting, braiding, felting, carding or twisting. Textile fibers may be natural or man-made in origin. Man-made textile fibers are made or modified by chemical processes that include spinning to convert polymer to fiber form and drawing to yield tensile properties needed to allow conversion of the textile fiber into yarn or fabric. Man-made textile fiber may be used as drawn, continuous filament textile fibers or such fibers can be cut into 2-10 cm lengths of staple textile fiber. In order to have sufficient strength for processing, most textile fibers have a diameter greater than about 10 microns or about 0.6 denier (weight in grams per 9,000 meters).

The textile fibers utilized to make the nonwoven web of the present invention are preferably drawn continuous filament textile fibers or staple fibers suitable for carding. The textile fibers of the invention may also comprise bicomponent fibers such as fibers having a sheath of one polymer surrounding a core of a second polymer wherein the sheath polymer has a lower melting point than the core polymer. The drawn continuous filament textile fibers of the present invention preferably have an average fiber diameter ranging between 10 and 55 microns. More preferably, the drawn continuous filament textile fibers have an average diameter ranging between 15 and 25 microns.

Several different methods for preparing drawn continuous filament textile fiber webs are known. Such methods generally comprise continuously extruding a thermoplastic polymer (either from a melt or a solution) through a spinneret in order to form discrete filaments, mechanically or pneumatically drawing the filaments without breaking to molecularly orient the polymer filaments and to achieve tenacity, and depositing the continuous filaments in a substantially random manner on a carrier belt to form a web of substantially continuous and randomly arranged, molecularly oriented filaments. Specific methods for making webs of drawn continuous filament textile fibers are described in U.S. Pat. Nos. 3,338,992 and 3,341,394 to Kinney, U.S. Pat. No. 3,276,944 to Levy, U.S. Pat. No. 3,502,538 to Peterson, U.S. Pat. Nos. 3,502,763 and 3,509,009 to Hartmann, U.S. Pat. No. 3,542,615 to Dobo et al., Canadian Pat. No. 803,714 to Harmon, U.S. Pat. No. 4,812,112 to Balk, U.S. Pat. No. 4,041,203 to Brock et al., U.S. Pat. No. 4,405,297 to Appel et al., and U.S. Pat. No. 4,753,834 to Braun et al. A preferred method for preparing webs of drawn continuous filament textile fibers is described in U.S. Pat. No. 3,692,618 to Dorschner et al.

The drawn continuous filament textile fibers of the invention can be selected from nylon fibers, polypropylene fibers, polyethylene fibers and polyester fibers.

Staple textile fibers suitable for carding are well known in the nonwoven fabric art. As described in *Man-made Fiber and Textile Dictionary*, published by Celanese, Inc., the carding process can be defined as a process wherein staple yarn is opened, cleaned, aligned and formed into a continuous unbonded web. This process utilizes a carding machine consisting of a series of rolls which are covered with card clothing which consists of wire teeth set in a foundation fabric or narrow serrated metal flutes which are spirally arranged around the roll. As the staple fibers move across these rolls, the wire teeth separate and align the fibers to yield a web of carded staple textile fibers.

The cardable staple textile fibers within the scope of the invention may be selected from polyester fibers, polypropylene fibers, polyethylene fibers, acrylic fibers, nylon fibers, or blends of these staple fibers. Cellulosic cardable staple textile fibers such as cotton or rayon or blends of such cellulosic fibers can also be used in the invention. However, cellulosic fibers may reduce the dryness of the nonwoven web of the invention.

The microfibers of the invention, made by the melt blowing process, preferably have an average fiber diameter of up to about 10 microns with very few, if any, of the fibers exceeding 10 microns in diameter. Usually the average diameter of the fibers will range from 2 to 6 microns. While it is possible to prepare fibers of average diameter larger than 10 microns by adjusting the conditions of the melt blowing process, these larger melt blown fibers are not preferred for use in the present invention. The smaller diameter fibers provide the coverage capacity necessary to highlight the differences between the regions of higher area density, which contain microfibers, and the regions of lower area density, which contain no microfibers. The microfibers are predominately discontinuous, however, they generally have a length exceeding that normally associated with staple fibers. Due to a reduced molecular orientation, these melt blown filaments will have a tenacity that is considerably lower than the drawn continuous textile fiber filaments.

Melt blown microfibers can be prepared by techniques well known in the art. As described in U.S. Pat. No. 4,041,203 to Brock et al., the method of forming melt blown fibers involves extruding a molten polymeric material into fine streams and attenuating the streams by opposing flows of high velocity, heated gas (usually air) to break the stream into discontinuous fibers of small diameter. Techniques for making blown fibers are also disclosed in an article entitled "Super Fine Thermo-Plastic Fibers" appearing in Industrial and Engineering Chemistry, Vol. 48, No. 8, pp. 1342-1346, and in U.S. Pat. Nos. 3,715,251, 3,704,198, 3,676,242, 3,595,245 and British Patent No. 1,217,892.

The melt blown microfibers of the present invention may be selected from polypropylene, polyethylene, poly(butylene terephthalate), poly(ethylene terephthalate), nylon 6, nylon 66, and copolymers of olefins such as polyethylene and polypropylene.

The polymeric nets of the present invention can be prepared as described in U.S. Pat. No. 4,636,419 to Madsen et al., which discloses several different methods for producing nets from thermoplastic polymers. Nets can be formed directly at the extrusion die or can be derived from extruded films by fibrillation or by embossment followed by stretching and splitting. A net with especially fine filaments can be prepared by the side-by-side extrusion of polymer streams, followed by the transversal embossment and splitting. The fine filaments of this net interlock with other types of fibers during the hydroentanglement process.

The polymeric nets of the present invention may be prepared from polyethylene, polypropylene, copolymers of polyethylene and polypropylene, poly(butylene terephthalate), poly(ethylene terephthalate), Nylon 6 and Nylon 66.

In accordance with the present invention, the nonwoven fabric of the invention comprising at least one layer of a web of textile fibers or net of polymeric filaments and a layer of a web of melt blown microfibers is combined together by hydroentangling. Hydroentangling generally refers to subjecting the fibers to a high velocity water jet to cause fiber entanglement between the textile fibers and melt blown microfibers causing these fibers to be bonded together into the nonwoven fabric. Although the term hydroentangling generally refers to the use of high pressure water to cause fiber entanglement, fluids other than water could also be utilized.

In accordance with the present invention, the small diameter high velocity jet streams of water which provide fiber entanglement also may function to create apertures in the nonwoven fabric. Depending on whether the textile fiber layer utilized has been prebonded prior to hydroentangling, a fabric having regions of higher area density and regions of lower area density may be obtained rather than a fabric having clean apertures. It is also within the scope of the present invention to provide a nonwoven web having apertures of two different sizes. It is further within the scope of the invention to provide a web comprising a layer of melt blown microfibers interposed between two layers of textile fibers.

In accordance with the invention, a process is provided for producing a nonwoven web comprising:
 supporting a first layer selected from a wed of textile fibers and a net of polymeric filaments and a second layer of a web of melt blown microfibers on an aperturing member; and
 impinging streams of high pressure liquid onto the fiber layers for a time sufficient to entangle the fibers with one another such that the fibers interlock to form a fabric. Generally, treatment with high pressure liquid streams is required on only one side of the fiber layers to achieve the fiber interlocking and pattern formation of the invention.

The process of the invention may also include the further step of calendering the fabric formed after hydroentanglement. The fabric formed by this process may be apertured or may have regions of higher area density and regions of lower area density. The process of the invention may also further comprise supporting a third layer comprising textile fibers over the second layer on the aperturing member prior to hydroentangling.

The aperturing member utilized to support the textile fiber layers during hydroentangling in accordance with the invention may be a wire or screen, a perforated plate, a three dimensional perforated plate, a perforated drum or a drum with a peripheral three-dimensional perforated surface. A perforated drum that may be used as the aperturing member within the scope of the present invention is described by U.S. Pat. No. 4,704,112 to Suzuki et al. The webs of melt blown and textile fibers are conveyed to the surface of the perforated drum. This drum may be a cylinder having predetermined diameter and length. The cylinder preferably has a repeating pattern of projections arranged on a smooth peripheral surface of the cylinder at predetermined spacing from one another and in the flat area defined among the projections, a plurality of perforations for drainage. Each of the projections is preferably configured so that the apertures may be formed in the web of melt blown microfibers and textile fibers with a high efficiency and the nonwoven fabric thus formed may be readily peeled off. The details of the projection design are more fully explained at column 5, lines 49–63 of Suzuki et al.

The wire or screen generally suitable for use as the aperturing member in the present invention may be of the type disclosed in "Forming Wires for Hydroentanglement Systems," *Nonwovens Industry*, 1988, pp. 39–43, Widen, C. B. and U.S. Pat. No. 3,485,706 to Evans. These screens may be woven from metal filaments or from filaments of thermoplastic polymers such as polyester or nylon.

In accordance with the present invention, a process is provided for producing a fabric having apertures of two different sizes. This process comprises:
 supporting a first layer selected from a web of textile fibers and a net of polymeric filaments and a second layer of a web of melt blown microfibers on a first aperturing member having aperturing means of a first size;
 impinging streams of high pressure liquid onto the fiber layers for a time sufficient to entangle the fibers with one another such that the fibers interlock to form a fabric having apertures of a first size;
 transferring the fabric to a second aperturing member having aperturing means of a second size; and
 impinging streams of high pressure liquid onto the fiber layers for a time sufficient to form apertures of a second size in the fabric. The process may further comprise supporting the layer of melt blown microfibers between two layers of textile fibers before and during hydroentanglement.

A nonwoven fabric having apertures of both larger and smaller sizes should possess liquid transport properties similar to those of fabrics having larger apertures while maintaining superior strength similar to that of webs having smaller apertures.

In accordance with the invention, a process is also provided for producing a nonwoven fabric comprising:
 extruding a web of drawn continuous filament textile fibers onto a continuous belt;
 extruding a web of melt blown microfibers onto the web of drawn continuous filament textile fibers on the continuous belt;
 transferring the webs onto an aperturing member; and
 impinging streams of high pressure liquid onto the fiber webs for a time sufficient to entangle the fibers with one another such that the fibers interlock to form a fabric.

As embodied in FIG. 1, a web of drawn continuous filament textile fibers can be prepared by extruding a thermoplastic polymer from extruder 12 through a plate 13 containing fine orifices into a chamber 14 where the molten fibers solidify. The fibers are strengthened by drawing them in tubes 15 filled with high velocity air. The fibers are deposited from tubes 15 onto foraminous continuous belt 16. U.S. Pat. No. 4,334,340 to Reba describes in detail a method for dispersing the drawn continuous filaments so that the dispersed filaments are capable of being deposited in a random, convoluted pattern, on foraminous continuous belt 16. Melt blown microfibers can be prepared by extruding a thermoplastic polymer from extruder 21 through melt blowing die 22, which deposits a web onto the web of drawn continuous filament textile fibers on foraminous continuous belt 16. It is to be understood that, in accordance with the invention, the melt blown microfibers could be deposited first on foraminous continuous belt 16 and the drawn continuous filament fibers could be deposited onto the melt blown microfibers.

Foraminous continuous belt 16 transfers the fiber layers onto an aperturing member such as wire 18. The aperturing member could also comprise a perforated drum, a perforated plate, a three-dimensional perforated plate or a drum with a peripheral three-dimensional perforated surface. The combination of fiber layers supported on the aperturing member pass under orifice water jet manifolds 23 which are positioned above the wire to discharge small diameter, high velocity jet streams of water onto the fiber layers. Each of manifolds 23 is connected to a source of water under pressure and each is provided, for example, with one or more rows of 0.005 inch diameter orifices spaces on 0.025 inch centers. The spacing between the orifice outlets of manifolds 23 and the webs directly beneath each manifold is preferably in the range from about $\frac{1}{4}$ inch to about $\frac{3}{4}$ inch. Water from jet manifolds 23 issuing from the orifices and passing through the webs and the aperturing wire is removed by vacuum boxes 24. Although only five manifolds 23 and five vacuum boxes 24 are illustrated by FIG. 1, it is to be understood that there is no limit to the number of manifolds 23 and vacuum boxes 24 which may be used. The first two of manifolds 23 preferably operate at a manifold pressure of about 200 psig and the remainder preferably operate at 600 psig to 1600 psig or higher.

Preparation of a pattern on the hydroentangled combination of textile fiber and microfiber webs, either apertures or regions of higher area density and regions of lower area density, is dependent on the configuration of the patterning wire carrying the webs through the hydroentangling process. As stated earlier herein, such patterning wire is disclosed by U.S. Pat. No. 3,485,706 to Evans and by Widen, "Forming Wires for Hydroentanglement System," *Nonwoven's Industry*, November 1988, pp. 39–43. The surface topography of the aperturing wire results from the particular pattern of the weave and the denier of the warp and the fill filaments making up the wire. At each point where the warp and fill filaments cross, a knuckle is formed. By proper choice of weave design and filament diameter, the height of these knuckles can be accentuated. During hydroentangling, the fibers are supported on the tops of these knuckles. The high velocity jet streams of water go through the web, hit the high wire knuckles and are deflected. The deflection of the water at the knuckle disrupts the web and forces the web fibers down from the high knuckles into the open or lower parts of the wire. An aperture or area of reduced fiber area density thus results. Apertures that are round, square, oval or rectangular (in either the machine or cross machine direction) can result depending on the wire design and wire filament shape and diameter.

After the hydroentangling/aperturing step, the composite fabric of melt blown microfibers and continuous filament textile fibers can be dried by methods that are well known in the nonwoven and paper manufacturing arts. The fabric can be dried by transporting it around the surface of hot cans such that water contained in the fabric is evaporated. A felt may be used to hold the apertured fabric against the hot drying cans. Use of a felt may control fabric shrinkage and improve water evaporation efficiency. Other methods of drying can also be utilized, such as infrared heating or through-air drying.

The nonwoven fabric of the invention may also optionally be calendered. A cold calender equipped with smooth rolls can be used to provide a smooth, soft, surface feel to the fabric. Alternatively, thermal bonding between filaments can be achieved if calendering is carried out between a hot smooth roll and a hot patterned roll. The bonding conditions of temperature, pressure, dwell time in the nip, and bonding pattern should be carefully selected to provide extra tensile strength without destroying softness and drape.

After the processing steps are completed, the nonwoven fabric of the invention can be wound by means of a winding apparatus into a roll ready for finishing steps such as slitting or shipment to the customer.

In accordance with the invention, another process is provided for producing a nonwoven web of the invention comprising, before the transferring and hydroentangling steps, the steps of:
 supplying a bonded web of drawn continuous filament textile fibers or a net of polymeric filaments to a continuous belt; and
 extruding a web of melt blown microfibers onto the bonded web of drawn continuous filament textile fibers or net of polymeric filaments on the continuous belt.

Figure 2:
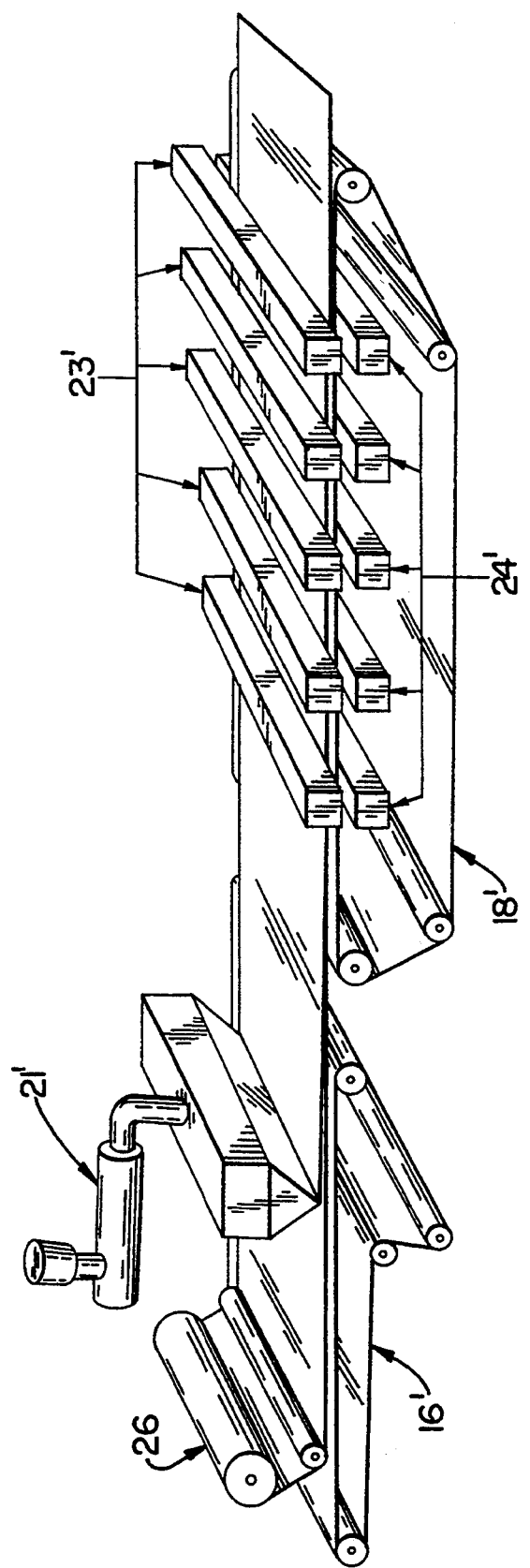
FIG. 2 is a schematic diagram illustrating a process of the invention for producing a nonwoven fabric by directly extruding melt blown microfibers onto a bonded web of drawn continuous filament fibers that have been bonded together, followed by hydroentangling.

As embodied in FIG. 2, the process is identical to that disclosed in FIG. 1 except that the drawn continuous filament textile fibers consist of a prebonded web, often called a spunbonded fabric. The preparation of spunbonded fabric begins with a process as described earlier herein wherein directly extruded, drawn continuous filament textile fibers are layered onto a foraminous belt. Bonding of such a web yields a spunbonded fabric. Several bonding techniques have been disclosed in the art to bond filaments of such fabrics together. Such techniques are selected depending on the particular polymer used and include techniques such as needle punching, hydroentangling, application of adhesives, application of heat and pressure to plasticize the fibers in the web and render them cohesive, and exposure to certain chemicals which can also plasticize and render the fibers cohesive.

The preferred method of bonding the drawn continuous filament textile fibers into a spunbonded fabric is by the use of heat and pressure, i.e., thermomechanical bonding. U.S. Pat. No. 4,753,834 to Braun et al. and U.S. Pat. No. 3,855,046 to Hansen et al. describe bonding a web made from drawn continuous filament textile fibers by passing the web between two bonding rolls, at least one of which, and preferably both of which, are heated. One roll has a smooth surface while the other roll includes an intermittent pattern of raised bosses on its surface. As the web passes between these two heated rolls, the web becomes stabilized by the formation of discrete compacted areas where fibers have been forced to cohere together by the action of heat and pressure. These bonds extend through a major portion of the web thickness and are distributed in an intermittent pattern corresponding to the bosses on the second roll. Unbonded filaments span the areas between bonds.

One factor to be considered in utilizing a spunbonded fabric is how the degree of bonding will influence the aperture/bonding properties of the combination of spunbonded fabric and melt blown microfibers during hydroentangling. As the degree and strength of the bonding in the spunbonded fabric is increased, the completeness of aperturing through the thickness of the melt blown/spunbonded fabric is reduced. Rather than clean apertures, a fabric having regions of higher area density and lower area density may be achieved after hydroentangling. Density as used in this context refers to weight per unit area. The areas of higher area density correspond to areas with a substantial quantity of both melt blown and spunbonded fibers. The areas of lower density correspond to areas where only spunbonded fibers can be observed. An apertured pattern is clearly apparent. However, upon close inspection a nonwoven web of the present invention may be formed with drawn continuous filament textile fibers bridging the apparent apertures. Such a nonwoven web gives the appearance of being apertured but in fact is not.

The spunbonded fabric can be supplied by means of an unwinding apparatus 26 onto foraminous continuous belt 16' as disclosed in FIG. 2. A web of melt blown microfibers is directly extruded by extruder 21' onto the spunbonded web on foraminous continuous belt 16'. The combination of spunbonded fabric and melt blown web is then conveyed to an aperturing member, shown as a wire 18' in FIG. 2. However, as in FIG. 1, the aperturing member can be any of those members described therein. After hydroentangling/aperturing, the composite fabric of melt blown and continuous filament textile fibers is then dried by means of, for instance, drying cans and then may be calendered by calender means and wound onto winding means. In accordance with the invention, a second spunbonded fabric may be further unwound onto the melt blown fiber web prior to hydroentangling.

Alternatively, unwinding apparatus 26 can be utilized to supply a net of polymeric filaments onto foraminous continuous belt 16, followed by extruding the web of melt blown microfibers onto the net.

As described in U.S. Pat. No. 4,636,419 to Madsen et al., several different methods for producing nets from thermoplastic polymers are known. Nets can be formed directly at the extrusion die or can be derived from extruded films by fibrillation or by embossment followed by stretching and splitting. A net with especially fine filaments can be prepared by the side-by-side extrusion of polymer streams, followed by the transversal embossment and splitting. The fine filaments of this net interlock with other types of fibers during the hydroentanglement process.

In accordance with the invention, a further process is provided for producing the nonwoven fabric of the invention comprising, before the transferring and hydroentangling steps, the steps of:
supplying a bonded web of carded staple textile fibers onto a continuous belt; and
extruding a web of melt blown microfibers onto the web of staple fibers on the continuous belt.

Carded staple textile fibers can be bonded together to give fabrics by methods described above for making spunbonded fabrics from webs of drawn continuous filament textile fibers. Bonding methods such as needle punching, hydroentangling, application of adhesives, thermomechanical bonding, or exposure to chemicals to plasticize could be utilized to provide the bonded carded web The degree of bonding used in the carded staple web must be sufficient to allow the fabric to be wound and unwound. The degree of bonding may also influence the aperturing/bonding of the combination of bonded carded staple web and melt blown microfibers during hydroentangling in much the same way as described above for spunbonded fabric.

In accordance with the invention, another process is provided for producing the nonwoven fabric of the invention comprising, before the transferring and hydroentangling steps, the steps of:
supplying a bonded web of textile fibers, a net of polymeric filaments or a fabric of bonded carded staple textile fibers onto a continuous belt; and
supplying a bonded web of melt blown microfibers onto the web of textile fibers, net of polymeric filaments or carded staple textile fibers on the continuous belt.

Premade webs of melt blown microfibers will possess some integrity due to entanglement of the individual fibers in the web as well as some degree of thermal or self bonding between the microfibers, particularly when collection is effected only a short distance after extrusion. Because of the generally low tensile strength of melt blown fibers, the degree of fiber bonding in the melt blown web will generally have little influence on the degree of aperturing (or separation into regions of higher area density and lower area density) which occurs after hydroentangling the combination of melt blown web and spunbonded fabric or bonded carded web.

Figure 3:
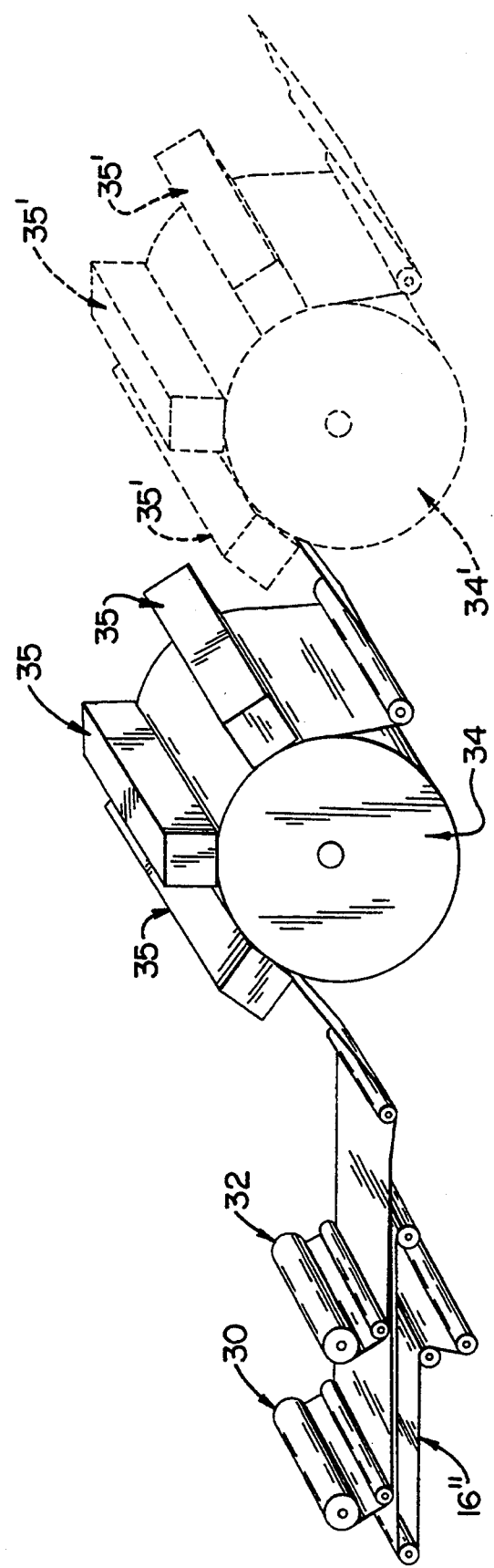
FIG. 3 is a schematic diagram illustrating a process of the invention for producing a nonwoven fabric by hydroentangling a premade web of melt blown microfibers laid onto a bonded web of drawn continuous filament fibers, a bonded web of carded staple textile fibers, or a polymeric net.

As embodied in FIG. 3, unwinding means 30 can be utilized to supply a fabric of bonded textile fibers, a net of polymeric filaments, or a fabric of bonded carded staple textile fibers onto foraminous continuous belt 16". Unwinding means 32 may also be utilized to supply the premade web of melt blown microfibers onto foraminous continuous belt 16". It is to be understood that, in accordance with the invention, the web of melt blown microfibers could be supplied first onto the continuous belt with the web of textile fibers then supplied onto the web of melt blown fibers. The combination of bonded textile fibers and melt blown microfiber webs is conveyed to an aperturing member which may be a perforated drum or a patterned wire. Use of a perforated drum 34 is shown in FIG. 3. Perforated drum 34 supports the fiber web so that hydroentangling using a stream of high pressure water may be conducted. Perforated drum 34 may be of the kind described by U.S. Pat. No, 4,704,112 to Suzuki et al. and described earlier herein. The entangling/aperturing of the present invention may be achieved by utilizing a single perforated drum 34 or may require a second entangling/aperturing drum such as described by Suzuki et al.

A series of orifice water jet manifolds 35 are arranged at predetermined intervals and opposed to the periphery of perforated drum 34. Orifice manifolds 35 discharge small diameter, high velocity Jet streams of water onto the web of melt blown and fabric of bonded textile fibers to provide fiber entanglement and simultaneously may also provide aperturing as the jet stream and the respective projections on the surface of perforated drum 34 interact to distribute the fibers. Each of manifolds 35 is connected with a source of water under pressure and each is provided with, for example, one or more rows of 0.005 inch diameter orifices spaced on 0.025 inch centers. The spacing between the orifice outlets of manifolds 35 and the web directly beneath each manifold 35 is preferably in the range from ¼ inch to about ¾ inch. Although only three manifolds 35 are illustrated in FIG. 3, it is to be understood that the number is limited only by the number that would fit around the circumference of perforated drum 34 and by the capacity of available suction means for suction drainage so that the efficiency of drainage on the outer surface of the aperturing drums can be maintained. The manifold pressure can operate at different levels, for example, the operating pressure of the initial manifold could be 200 psig and the remainder of the manifolds at 600 psig to 1600 psig or higher.

After the hydroentangling/aperturing step, step web of melt blown and fabric of bonded textile fibers can be dried by methods that are well known in the nonwoven and paper manufacturing arts. Drying can be accomplished by moving the apertured web around the surface of hot drying cans such that water contained in the web is evaporated. A felt may be used to hold the apertured fabric against the hot drying cans. Use of a felt may control fabric shrinkage and improve water evaporation efficiency. Other methods of drying can also be utilized, such as infrared heating or through-air drying.

The nonwoven fabric of the invention may also optionally be calendered. A cold calender equipped with smooth rolls can be used to provide a smooth, soft, surface feel to the fabric. Alternatively, thermal bonding between web filaments can be achieved if calendering is carried out between a hot smooth roll and a hot patterned roll. The bonding conditions of temperature, pressure, dwell time in the nip, and bonding pattern may be carefully selected to provide extra tensile strength without destroying softness and drape.

After the processing steps are completed, the nonwoven fabric of the invention can be wound by means of a winding apparatus into a roll ready for finishing steps such as slitting or shipment to the customer.

Figure 4:
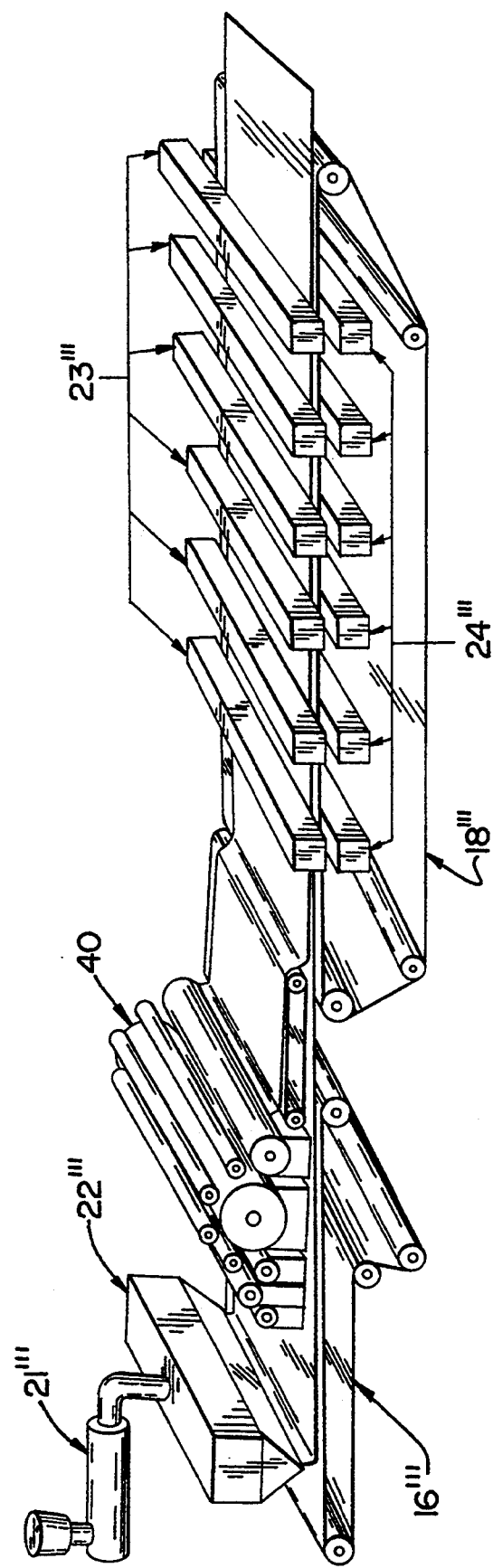
FIG. 4 is a schematic diagram illustrating a process of the invention for producing a nonwoven fabric by carding a web of staple fibers on a directly extruded web of melt blown microfibers, followed by hydroentangling.

In accordance with the invention, as illustrated in FIG. 4, a further process is provided for producing the nonwoven web of the invention comprising, before the transferring and hydroentangling steps, the steps of:
  extruding or supplying a web of melt blown microfibers onto a continuous belt; and
  carding a web or supplying a bonded carded web of staple textile fibers onto the web of melt blown microfibers on the continuous belt.

The process of producing a web of carded staple textile fibers is well known in the art and is described earlier herein. The carding process will normally yield a given weight of material at a slower rate than the hydroentangling process is usually operated. Thus, as embodied in FIG. 4, it may be necessary for more than one carded web-forming apparatus 40 to be utilized such that the carded web layers produced are sufficient to produce the nonwoven web of the invention.

The web of melt blown microfibers is extruded by extruder 2140 ″ through melt blowing die 22‴ onto foraminous continuous belt 16‴. The carded web from the web-forming apparatus 40 is laid onto the web of melt blown microfibers on foraminous continuous belt 16‴. In accordance with the invention, the web can be carded directly onto the web of melt blown microfibers or can be carded and bonded prior to being supplied as a roll onto the melt blown web.

When a bonded web of carded staple fibers is used on top of the melt blown web during the aperturing process, the attachment of the two layers of fibers is not as strong as when the bonded carded web is on the bottom. However, when the bonded carded web is on top, the surface texture of the carded web is preserved in the apertured fabric. When the bonded carded web is on the bottom, the entanglement is more complete and the fine microfibers of the melt blown web tend to dominate the tactility of the apertured fabric.

The combined web of carded staple textile fibers and melt blown microfibers is then conveyed to an aperturing member which may be a wire 18‴ or any of the other aperturing members disclosed earlier herein. After hydroentangling/aperturing the melt blown microfibers and carded staple textile fibers, the resulting fabric may be dried by drying cans or other suitable means as disclosed earlier herein, and then may be calendered by calender means and wound onto a roll by winding means as disclosed earlier herein. Within the scope of the invention, the process for producing the nonwoven fabric of the invention may further comprise carding a web of staple textile fibers on foraminous continuous belt 16‴ prior to depositing the web of melt blown microfibers, followed by carding a second web onto the melt blown web. In such a configuration, the melt blown web would be between the two carded webs before and during the hydroentangling process.

In accordance with the invention, a further process is provided for producing the nonwoven fabric of the invention comprising, before the transferring and hydroentangling steps, the steps of:
  carding a web of staple textile fibers onto a continuous belt; and
  extruding or supplying a web of melt blown microfibers onto the carded web of staple textile fibers on the continuous belt.

In accordance with the invention, a process is also provided for producing a nonwoven fabric comprising, before the transferring and hydroentangling steps, the steps of:
  extruding a web of drawn continuous filament textile fibers onto a continuous belt; and
  supplying a bonded web of melt blown microfibers onto the web of drawn continuous filament textile fibers on the continuous belt.

In accordance with the invention, the nonwoven fabric of the present invention may be utilized in an diaper or sanitary napkin. When utilized in a diaper, the nonwoven web of the invention can function as a topsheet layer in contact with the wearer's skin. The diaper comprises at least a topsheet layer, a layer of an absorbent material and an impermeable outer covering.

In accordance with the invention, if the nonwoven fabric of the invention having regions of higher area density and regions of lower area density is utilized as the diaper topsheet, it may be desirable to treat the topsheet with a hydrophilic surfactant material, such as Triton X-100, to enable liquid to penetrate the topsheet layer. It may also be desirable to utilize within the diaper a super-absorbent polymer. An aesthetically pleasing diaper with good strike-through and rewet properties can be achieved by using a surfactant treated nonwoven web of this invention having regions of higher area density and regions of lower area density as a diaper topsheet and using a super-absorbent polymer as at least part of the absorbent material in the diaper.

The following working Examples are provided to illustrate the present invention and some of its advantages. The Examples are in no way limitative of the present invention.

EXAMPLES

The examples were prepared using the applicants' pilot hydroentangling apparatus. This apparatus includes a water jet manifold and a movable foraminous surface which travels beneath the water jet manifold.

As used herein, the expression "GSY" means grams per square yard, "DPF" means denier per filament, "PLI" means pounds per lineal inch, and "PSI" means pounds per square inch.

The samples listed in Table I were produced as follows: a web of textile fibers was laid on the movable foraminous forming screen of the hydroentangling pilot unit A web of melt blown microfibers was then placed on the web of textile fibers.

In some experiments, a second layer of textile fibers was then added onto the web of melt blown microfibers to make a textile fiber plus microfiber composite. The forming screen used for each sample has the indicated number of strands per inch in the machine and cross directions listed in Table I. The combination of textile fiber and microfiber webs were hydroentangled together by moving the forming screen beneath the high-pressure jet manifold. Table I lists the number of manifold treatments and the corresponding water pressure in the nozzles to provide the entangling energy with each treatment. After the indicated number of treatments at the listed water pressure, the apertured topsheet of the invention was allowed to dry. In some of the experiments, the product was then subjected to post-treatments of cold or hot calendering.

The textile fiber webs and melt blown microfiber webs used to make the examples are listed in Table I under the title "Formulation."

Example 1

For Example 1, the textile fiber web used was CEREX ® Type 29 spunbond Nylon 66 product (sold by James River Corporation, Greenville, S.C.) having a basis weight of 8.4 GSY. The microfiber web used was POLYWEB ® polypropylene melt blown fabric (sold by James River Corporation, Greenville, S.C.) having a basis weight of 8.5 GSY. The textile fiber web was made by the process described in U.S. Pat. No. 3,542,615 to Dobo et al.

The melt blown microfiber web was made as generally described above by the melt blowing process, well known in the art, using polypropylene polymer. The webs of spunbond textile fibers and melt blown microfibers were then hydroentangled together using the hydroentangling pilot unit operated as described above with process conditions listed in Table 1. The resulting product of the invention, having a clearly visible pattern of regions of higher area density and regions of lower area density, is characterized in Table 2.

Examples 2-6

Examples 2-6 were made using CEREX ® Type 29 spunbond Nylon 66 textile fiber web, basis weight 8.4 GSY, and POLYWEB ® poly (butylene terephthalate) melt blown microfiber web, basis weight 23 GSY (sold by James River Corporation, Greenville, S.C.). The webs of spunbond textile fibers and melt blown microfibers were hydroentangled together using the hydroentangling pilot unit operated as described above with process conditions listed in Table 1. The resulting products are characterized in Table 2.

Example 7

Example 7 illustrates the combination of carded webs of polyester textile fibers and polyester melt blown microfibers to make products of this invention. Poly (ethylene terephthalate) textile fiber, 1.5 denier per filament, 1.5 inches cut length (sold by E. I. du Pont de Nemours as product Code 113D03) was carded into a web with basis weight 17 grams per square yard. A web of melt blown microfiber, POLYWEB ® poly (butylene terephthalate), basis weight 36 grams per square yard (sold by James River Corporation, Greenville, S.C.) was laid on the above described carded polyester textile fiber web. A second section of the above described carded polyester textile fiber web was then placed over the web of melt blown microfibers. The combination of carded textile fiber and melt blown microfiber webs was then hydroentangled together using the hydroentangling pilot unit operated as described above with process conditions listed in Table 1. The resulting product of this invention is characterized in Table 2.

Examples 8 and 9

Examples 8 and 9 illustrate the combination of two spunbond textile webs to cover both the top and bottom of the web of melt blown microfibers. These examples were made using CELESTRA ® IV polypropylene spunbond webs of basis weight 12 grams per square yard or 17 grams per square yard sold by James River Corporation, Greenville, S.C. and a web of melt blown microfibers, POLYWEB ® polypropylene with basis weight 17 grams per square yard (sold by James River Corporation, Greenville, S.C.). The combination of spunbond textile and melt blown microfiber webs were then hydroentangled together using the hydroentangling pilot unit operated as described above with process conditions listed in Table 1. The resulting products of the invention are characterized in Table 2.

Example 10

Example 10 illustrates the combination of carded web polypropylene textile fibers and polypropylene melt blown microfibers to make products of the invention. Polypropylene textile fibers—two denier per filament, 1.5 inches cut length (sold by Hercules Corporation, Norcross, Ga. as product Code T199) was carded into a web with basis weight of 17 grams per square yard. A web of melt blown microfibers, POLYWEB ® polypropylene basis weight 17 grams per square yard (sold by James River Corporation, Greenville, S.C.) was covered above and below with the above described web of polypropylene textile fibers. The combination of carded textile fiber and melt blown microfiber webs were then hydroentangled together using the hydroentangling pilot unit operated as described above with process condition listed in Table 1. The resulting product of the invention is characterized in Table 2.

Example 11

Example 11 illustrates the combination of carded webs of polypropylene textile fibers and poly (butylene terephthalate) melt blown microfibers to make products of the invention. This product was made as described above for Example 10, but POLYWEB ® poly (butylene terephthalate) melt blown microfibers, 36 grams per square yard (sold by James River Corporation, Greenville, S.C.), was used. Table 1 lists hydroentangling details. The resulting product of this invention is characterized in Table 2.

Example 12

Example 12 was made as described above for Example 7. Note in Table 1 that a 100×100 screen was used for hydroentangling. This very fine screen will yield a product with a pattern of regions of higher area density and regions of lower area density only visible under magnification. Example 12 is characterized in Table 2.

Example 13

Example 13 illustrates the combination of two linear low density polyethylene (LLDPE) spunbond textile webs to cover both the top and the bottom of the web of melt blown microfibers. Spunbond textile webs made using LLDPE are made as generally described above using linear low density polyethylene (available from Dow Chemical) as the polymer to spin. The resulting drawn continuous filament textile fibers were bonded together using heat and pressure developed in a nip between a smooth steel roll and an embossed pattern roll to yield approximately 18% bonded area and approximately 160 bonds per square inch. The resulting spunbond LLDPE CELESTRA ® I type web, basis weight of 23 grams per square yard, was placed above and below a web of melt blown microfiber, POLYWEB ® poly (butylene terephthalate) with basis weight 36 grams per square yard (sold by James River Corporation, Greenville, S.C.). This combination of spunbond textile and melt blown microfiber webs was then hydroentangled together using the hydroentangling pilot unit operated as described above with process conditions listed in Table 1. The resulting product of the invention is characterized in Table 2.

Example 14

Example 14 illustrates the combination of a polymer net and a web of melt blown microfibers. The polymer net is manufactured by the Kaysersberg Division of Begbin-Say Corporation of France and is called SCRINYL ®. The process used to manufacture this net is described in U.S. Pat. No. 4,636,419. The net has two polymer components—nylon in the filaments and polypropylene in the matrix—and has a basis weight of 10 g/yd$^2$ The melt blown microfiber web is prepared from poly (butylene terephthalate) with basis weight 10 g/yd$^2$ (sold by James River Corporation, Greenville, S.C.). The polymer net was placed on an 8×6 screen which was mounted on the hydroentangling pilot unit. The melt bloom web was placed on top of the polymer net. The hydroentangling pilot unit was operated with the process conditions listed in Table 1. The resulting product is characterized in Table 2.

Example 15

Example 15 was made using CEREX ® Type 30 spunbond Nylon 66 textile fiber web, basis weight 8.4 GSY and POLYWEB ® (polybutylene terephthalate) melt blown microfiber web, basis weight 13 GSY (sold by James River Corporation, Greenville, S.C.). CEREX ® Type 30 is made as described for CEREX ® Type 29 in Example 1, except the drawn continuous filament textile fibers are thermally bonded in passing through a nip formed by a heated smooth steel roll and a heated pattern roll. The webs of spunbond textile fibers and melt blown microfibers were then hydroentangled together using the hydroentangling pilot unit operated as described above with process conditions listed in Table 1. The resulting product of this invention had a clearly visible pattern of regions of higher area density and regions of lower area density.

Figure 5A:
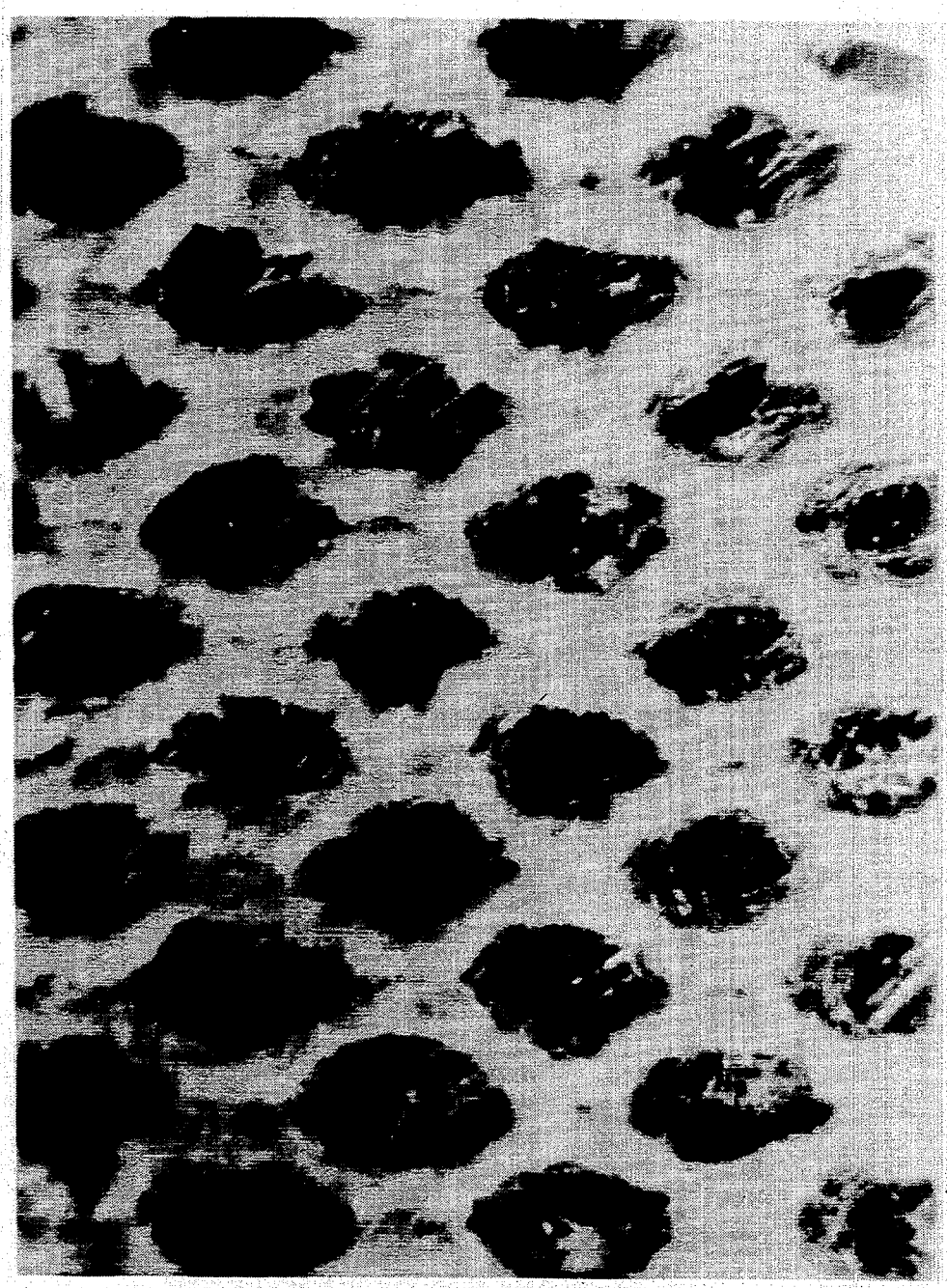
FIGS. 5A, 5B and 5C show three views of the melt blown microfiber side of the product produced by Example 15 with a 7X, 10X and 15X magnification, respectively.
Figure 5B:
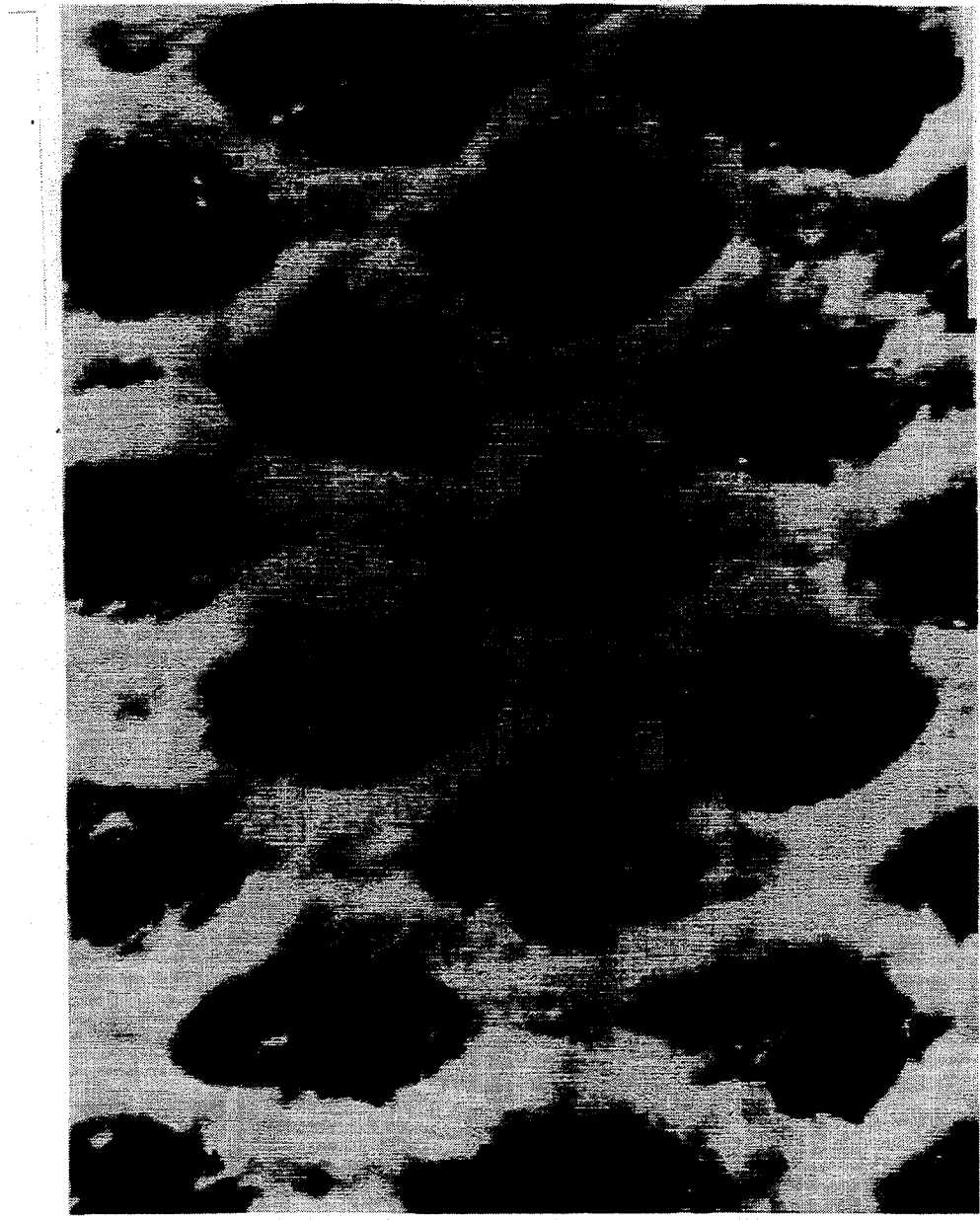
Figure 5C:

The structure produced by Example 15 was characterized via photographic analysis. FIG. 5 shows several views of the melt blown microfiber side of this structure at 7X, 10X and 15X magnification. A pattern of apparent apertures is clearly visible which results from regions of higher area density spunbond textile fibers plus melt blown microfibers, and regions of lower area density, spunbond textile fibers only. The apparent apertures have dimensions of 2.1 mm×1.3 mm.

Figure 6A:
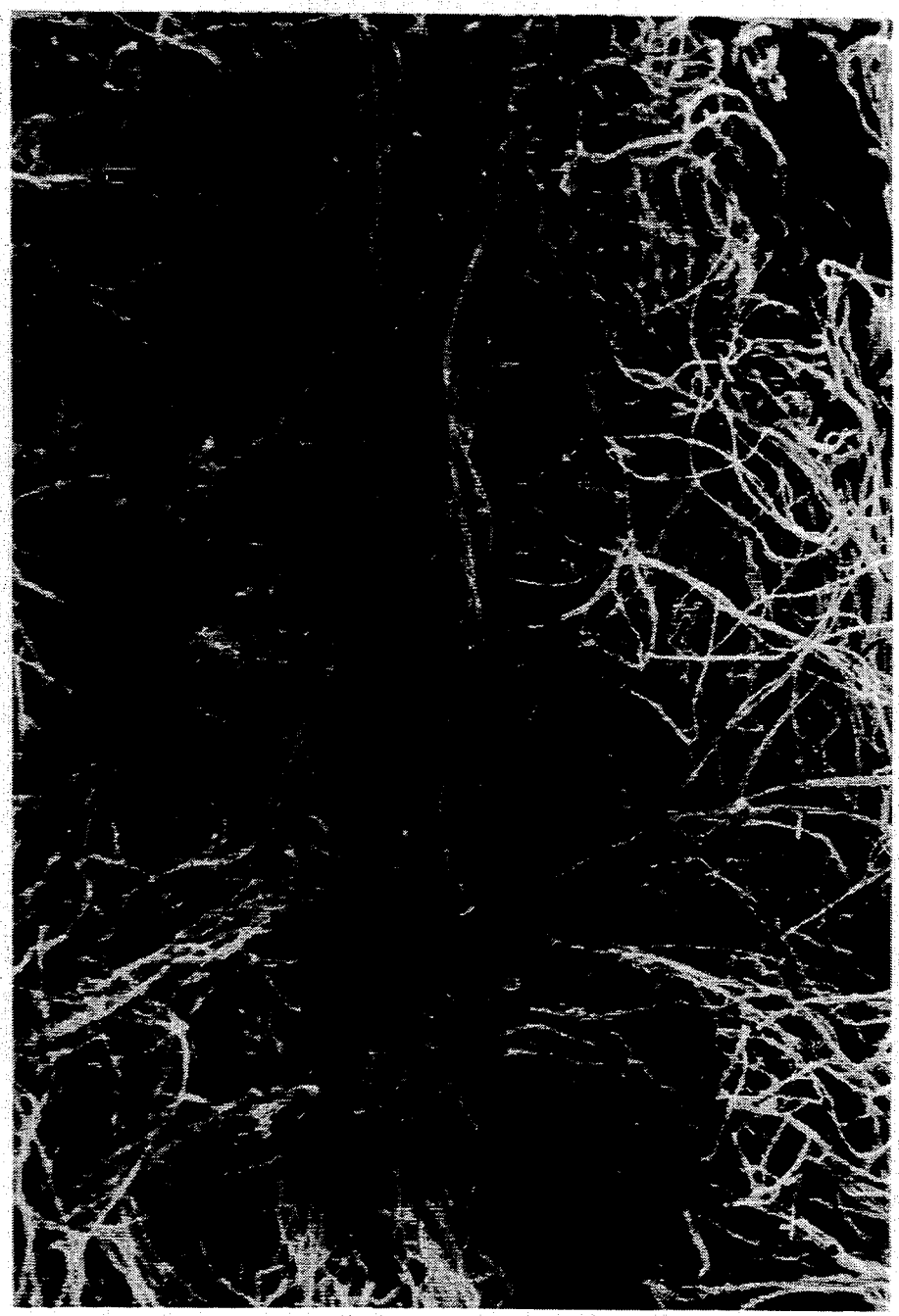
FIG. 6A provides a view of a region of higher area density of the microfiber side of the product produced by Example 15 at 100X magnification via scanning electron microscopy (SEM).
Figure 6B:
FIG. 6B provides a view of a region of lower area density of the microfiber side of the product produced by Example 15 at 100X magnification via scanning electron microscopy (SEM).

A second view of the microfiber side of Example 15 is provided by Scanning Electron Microscopy (SEMI photographs at 100X magnification shown as FIGS. 6A and 6B. FIG. 6A, showing a region of higher area density, illustrates how the very low denier melt blown microfibers cover the spunbond textile fibers to yield the white dense bond areas seen as the fabric pattern background. FIG. 6B, showing a region of lower area density, illustrates how the apparent aperture is actually mostly bridged by the textile fibers making up the spunbond web. Part of a thermal bond holding the drawn continuous filament textile fibers in the spunbond web is also visible in the apparent aperture.

Figure 7B:
FIG. 7B provides a view of a region of lower area density of the spunbond web side of the product produced by Example 15 at 100X magnification via SEM.
Figure 7C:
FIG. 7C provides a view of a region of lower area density of the spunbond web side of the product produced by Example 15 at 75X magnification via SEM.

A view of the spunbond web side of Example 15 is provided by SEM photographs at 100X magnification shown as FIGS. 7A, 7B and 7C. FIG. 7A, showing a region of higher area density, illustrates how the melt blown microfibers are mixed into the spunbond textile fiber web to anchor the total structure together. FIGS. 7B and 7C, showing regions of lower area density, illustrate how the apparent aperture can be bridged with filaments and with nearly undamaged bond sites from the spunbond web.

Figure 8A:
FIG. 8A provides a cross-sectional view of the product produced by Example 15 at 200X magnification via SEM.

FIG. 8 provides cross-sectional views of Example 15 via SEM photography at 100X magnification. Mixing of the melt blown microfibers into the spunbond textile fibers, resulting from the action of the hydroentangling process, is again illustrated.

The photographs in FIGS. 5–8 clearly illustrate the unique structure of Example 15, a product of this invention, including the pattern of apparent apertures resulting from regions of higher and lower area density, and the two-sidedness resulting from combining a web of melt blown microfibers and a web of bonded drawn continuous filament textile fibers.

Example 16

Example 16 was made using CEREX ® Type 30 spunbond Nylon 66 textile fiber web, basis weight 8.4 GSY and POLYWEB ® (polybutylene terephthalate) melt blown microfiber web, basis weight 12.5 GSY (sold by James River Corp., Greenville, S.C.). The webs of spunbond textile fibers and melt blown microfibers were then hydroentangled together as in Example 15.

Comparative Example 1

Comparative Example 1 in Table 2 is a prior art non-apertured nonwoven fabric sold as a diaper liner by James River Corporation. This fabric was produced by thermal calendering a carded web of polypropylene fiber having a denier of 2.

Examples 1–16 and Comparative Example 1 described above are characterized in Table 2. Following is a description of the test methods used to evaluate these products. Note that in several tests the topside of the product and the bottom side of the product were each evaluated. Table 2 results labeled "Up" refer to testing of the melt blown microfiber side of the product. Results labeled "Down" refer to testing of the textile fiber or polymer net side of the product.

BASIS WEIGHT

Following is a description of the test methods used to evaluate the products described in the Examples.

Basis weight was determined by measuring the weight of a known area of fabric. The result, reported as grams per square yard ("GSY"), is the average of at least 4 measurements.

STRIP TENSILE STRENGTH

Strip tensile strength was evaluated by breaking a one-inch by seven-inch long sample generally following ASTM D168264, the One-Inch Cut Strip Test. The instrument cross-head speed was set at 5 inches per minute and the gauge length was set at 5 inches. The tensile strength in both the machine direction ("MD") and cross direction ("CD") was evaluated. The Strip Tensile Strength or breaking load, reported as grams per inch, is the average of at least 8 measurements.

STRIP ELONGATION

Strip elongation was evaluated at the same time as Strip Tensile Strength and represents the percent increase in fabric length observed at break while generally following ASTM D 1682-64, the One Inch Cut Strip Test.

CALIPER (UNDER COMPRESSION)

Caliper was determined by measuring the distance between the top and the bottom surface of the sheet while the sheet was held under compression loading of 19 grams per square inch or 131 grams per square inch. The result, reported in mils, is the average of 10 measurements.

STRIKE-THROUGH

Strike-through was evaluated by a method similar to that described in U.S. Pat. Nos. 4,391,869 and 4,041,451. Strike-through was measured as the time for 5 milliliters of synthetic urine solution placed in the cavity of the strike-through plate to pass through the Example Fabric into an absorbent pad. The result, reported in seconds, is generally the average of 4 tests.

SURFACE WETNESS (Rewet)

Surface Wetness was evaluated by a method similar to that described in U.S. Pat. Nos. 4,041,951 and 4,391,861. Surface Wetness, reported in grams, was evaluated by adding synthetic urine through the Example Fabric into the absorbent pad until the absorbent pad was nearly saturated. Thus the Example Fabric was wet at the beginning of the Surface Wetness test. For results denoted as "Rewet 0.5 PSI," the loading factor was slightly less than 4 (grams of synthetic urine per gram of absorbent sample). A uniform pressure loading of 0.5 psi was then applied and the procedure concluded as disclosed in the above patents. For results denoted as "Rewet 1.0 PSI," the loading factor was increased to slightly over 4 so the absorbent pad was saturated with synthetic urine. A uniform pressure loading of 1.0 psi was then applied and the procedure concluded as disclosed in the above patents. The result, reported in grams, is generally the average of 4 tests.

SOFTNESS

Softness was evaluated by an organoleptic method wherein an expert panel compared the surface feel of Example Fabrics with that of controls. Results are reported as a softness score with higher values denoting a more pleasing hand. Each reported value is for a single test sample but reflects the input of several panel members.

Illustrated results in Table 2 demonstrate that many properties of the apertured topsheet of the invention are similar or better than properties of the prior art non-apertured topsheet listed as "Comparative" Example 1 in Table 2.

The liquid transport properties for the COMPARATIVE and the products of the invention do not reflect the effect of a "spacer or wicking" layer under them. In actual practice, such a material would be useful to achieve optimum performance.

Test diapers were made using the topsheet of the invention exemplified by Example 16. Consumers (n=32) in an in-home use test preferred the test diapers and rated the test diapers as superior relative to a major competitor for liner related features and benefits. These results were significant at the 95%, confidence level. The competitor diapers used in this study were made utilizing a thermally bonded carded polypropylene topsheet very similar to that described in Comparative Example 1.

Although the present invention has been described in connection with the preferred embodiments, it is to be understood that modifications and variations may be resorted to without departing from the spirit and scope of the invention. Such modifications are considered to be within the purview and scope of the invention and the appended claims.

TABLE 1

| | PREPARATION OF FABRIC SAMPLES | | | |
|---|---|---|---|---|
| EX-AMPLE | FORMULATION | APERTURING SCREEN | HYDROENTANGLING CONDITIONS NUMBER OF MANIFOLD TREATMENTS AT LISTED HYDRAULIC PRESSURE | POST TREATMENT |
| 1 | 8.4 GSY SPUNBOND NYLON CEREX$^R$(TYPE 29) + 8.5 GSY POLYPROPYLENE MELTBLOWN MICROFIBER | 13 × 20 | 2 @ 200 PSI<br>2 @ 1200 PSI<br>2 @ 1600 PSI | COLD CALENDERED |
| 2 | 8.4 GSY SPUNBOND NYLON CEREX$^R$(TYPE 29) + 23 GSY POLYBUTYLENE TEREPHTHALATE MELTBLOWN MICROFIBER | 8 × 8 | 2 @ 200 PSI<br>6 @ 800 PSI<br>4 @ 1200 PSI<br>2 @ 1600 PSI | COLD CALENDERED |
| 3 | AS 2 | 10 × 10 | 2 @ 200 PSI<br>6 @ 800 PSI<br>6 @ 1200 PSI | COLD CALENDERED |

TABLE 1-continued
PREPARATION OF FABRIC SAMPLES

| EXAMPLE | FORMULATION | APERTURING SCREEN | HYDROENTANGLING CONDITIONS NUMBER OF MANIFOLD TREATMENTS AT LISTED HYDRAULIC PRESSURE | POST TREATMENT |
|---|---|---|---|---|
| 4 | AS 2 | 31 × 25 | 2 @ 200 PSI<br>6 @ 800 PSI<br>6 @ 1200 PSI<br>4 @ 1600 PSI | COLD CALENDERED |
| 5 | AS 2 | 13 × 20 | 2 @ 200 PSI<br>4 @ 800 PSI<br>4 @ 1600 PSI | COLD CALENDERED |
| 6 | AS 2 | 12 × 12 | 2 @ 200 PSI<br>4 @ 800 PSI<br>4 @ 1600 PSI | COLD CALENDERED |
| 7 | 17 GSY CARDED WEB OF 1.5 DPF DUPONT POLYESTER TEXTILE FIBER + 36 GSY POLYBUTYLENE TEREPHTHALATE MELTBLOWN MICROFIBER + 17 GSY CARDED WEB OF 1.5 DPF DUPONT POLYESTER TEXTILE FIBER | 13 × 20 | 2 @ 200 PSI<br>2 @ 800 PSI<br>10 @ 1400 PSI | NONE |
| 8 | 12 GSY SPUNBOND POLYPROPYLENE CELESTRA IV + 17 GSY POLYPROPYLENE MELT BLOWN + 12 GSY SPUNBOND POLYPROPYLENE CELESTRA IV | 13 × 20 | 2 @ 200 PSI<br>2 @ 800 PSI<br>10 @ 1400 PSI | NONE |
| 9 | 20 GSY SPUNBOND POLYPROPYLENE CELESTRA IV + 17 GSY POLYPROPYLENE MELTBLOWN + 20 GSY SPUNBOND POLYPROPYLENE CELESTRA IV | 13 × 20 | 2 @ 200 PSI<br>2 @ 800 PSI<br>10 @ 1800 PSI | NONE |
| 10 | 17 GSY CARDED WEB OF 2 DPF POLYPROPYLENE TEXTILE FIBER + 17 GSY POLYPROPYLENE MELTBLOWN + 17 GSY CARDED WEB OF 2 DPF POLYPROPYLENE TEXTILE FIBER | 13 × 20 | 2 @ 200 PSI<br>2 @ 800 PSI<br>10 @ 1400 PSI | NONE |
| 11 | 17 GSY CARDED WEB OF 2 DPF POLYPROPYLENE TEXTILE FIBER + 36 GSY POLYBUTYLENE TEREPHTHALATE MELTBLOWN + 17 GSY CARDED WEB OF 2 DPF POLYPROPYLENE TEXTILE FIBER | 13 × 20 | 2 @ 200 PSI<br>2 @ 800 PSI<br>10 @ 1800 PSI | NONE |
| 12 | 17 GSY CARDED WEB OF 1.5 DPF DUPONT POLYESTER TEXTILE FIBER + 36 GSY POLYBUTYLENE TEREPHTHALATE MELTBLOWN + 17 GSY CARDED WEB OF 1.5 DPF DUPONT POLYESTER TEXTILE FIBER | 100 × 100 | 2 @ 200 PSI<br>2 @ 800 PSI<br>10 @ 1400 PSI | NONE |
| 13 | 23 GSY SPUNBOND LLDPE CELESTRA I + 36 GSY POLYBUTYLENE TEREPHTHALATE MELTBLOWN + 23 GSY SPUNBOND LLDPE CELESTRA I | 13 × 20 | 2 @ 200 PSI<br>2 @ 800 PSI<br>10 @ 1400 PSI | NONE |
| 14 | 10 GSY SCRINYL POLYMER NET + 10 GSY POLYBUTYLENE TEREPHTHALATE MELTBLOWN MICROFIBER | 8 × 6 | 2 @ 200 PSI<br>4 @ 800 PSI<br>4 @ 1000 PSI | NONE |
| 15 | 8.4 GSY SPUNBOND NYLON CEREX$^R$ (TYPE 30) + 13 GSY POLYBUTYLENE TEREPHTHALATE MELTBLOWN MICROFIBER | 13 × 20 | 2 @ 200 PSI<br>4 @ 800 PSI<br>6 @ 1200 PSI | NONE |
| 16 | 8.4 GSY SPUNBOND NYLON CEREX$^R$ (TYPE 30) + 12.5 GSY POLYBUTYLENE TEREPHTHALATE MELTBLOWN MICROFIBER | 8 × 6 | 2 @ 400 PSI<br>2 @ 800 PSI<br>6 @ 1200 PSI | NONE |

TABLE 2
PROPERTIES OF HYDROENTANGLED FABRICS

| EXAMPLE | BASIS WEIGHT | STRIP TENSILE | | STRIP ELONGATION | | SOFTNESS | |
|---|---|---|---|---|---|---|---|
| | | MD | CD | MD | CD | UP(1) | DOWN(2) |
| Comparative Example 1 | 20 | 1500 | 300 | — | — | 80 | — |
| 1 | 25 | 700 | 170 | 130 | 115 | 70 | 50 |
| 2 | 34 | 1430 | 630 | 107 | 97 | 82 | 68 |
| 3 | 33 | 1300 | 630 | 85 | 90 | 75 | 78 |
| 4 | 34 | 1540 | 760 | 107 | 81 | 90 | 80 |
| 5 | 34 | 1430 | 1200 | 83 | 100 | 60 | 68 |
| 6 | 35 | 1320 | 680 | 69 | 90 | 78 | 65 |
| 7 | 60 | 2055 | 1185 | 79 | 95 | — | 65 |
| 8 | 43 | 3046 | 977 | 76 | 69 | — | 72 |
| 9 | 59 | 4909 | 1657 | 49 | 82 | — | 65 |
| 10 | 46 | 879 | 644 | 100 | 124 | — | 65 |
| 11 | 70 | 1875 | 1078 | 111 | 124 | — | 42 |
| 12 | 63 | 3080 | 1425 | 64 | 98 | — | 90 |

TABLE 2-continued

| PROPERTIES OF HYDROENTANGLED FABRICS | | | | | | | |
|---|---|---|---|---|---|---|---|
| 13 | 90 | 2525 | 1263 | 168 | 112 | — | 72 |
| 14 | 20 | 2054 | 3133 | 20 | 7 | — | — |
| 15 | PRODUCT STRUCTURE CHARACTERIZED VIA PHOTOGRAPHY | | | | | | |
| 16 | 25 | 2054 | 517 | 37 | 60 | 60 | 95 |

| EXAMPLE | CALIPER (MIL) | | STRIKE-THROUGH | | REWET 0.5 PSI | | REWET 1.0 PSI | |
|---|---|---|---|---|---|---|---|---|
| | 19 G/IN2 | 131 G/IN2 | UP(1) | DOWN(2) | UP(1) | DOWN(2) | UP(1) | DOWN(2) |
| Comparative Example 1 | 18 | 10 | 2.0 | — | 0.11 | — | 1.0 | — |
| 1 | 19 | 12 | 4.9 | 4.8 | 0.28 | 0.23 | 1.2 | 1.2 |
| 2 | 12 | 8.0 | 10.7 | 7.4 | 0.4 | 1.4 | 2.1 | 3.0 |
| 3 | 11 | 8.0 | 6.3 | 6.3 | 2.0 | 2.3 | 1.2 | 1.2 |
| 4 | 12 | 9.0 | 20.5 | 17 | 1.5 | 2.4 | 3.2 | 3.8 |
| 5 | 11 | 8.7 | 4.2 | 4.7 | 1.8 | 1.4 | 3.0 | 3.3 |
| 6 | 12 | 9.1 | 6.8 | 5.8 | 1.1 | 1.2 | 3.0 | 2.8 |
| 7 | 58 | 32(3) | — | 6.2 | — | 0.07 | — | — |
| 8 | 33 | 16(3) | — | — | — | — | — | — |
| 9 | 40 | 25(3) | — | — | — | — | — | — |
| 10 | 37 | 28(3) | — | 5.2 | — | 0.06 | — | — |
| 11 | 52 | 31(3) | — | — | — | — | — | — |
| 12 | 37 | 18(3) | — | — | — | — | — | — |
| 13 | 45 | 25(3) | — | — | — | — | — | — |
| 14 | — | — | 3.2 | — | — | — | — | — |
| 15 | | | | | | | | |
| 16 | 12 | 9 | — | 4.2 | 0.84 | 0.66 | — | — |

(1)UP SIDE IS MELTBLOWN MICROFIBER SIDE.
(2)DOWN SIDE IS TEXTILE FIBER SIDE.
(3)LOADING WAS 107 G/IN2.

What is claimed is:

1. A process for producing a nonwoven composite fabric having apertures of two different sizes, comprising:
supporting a first layer selected from a web of textile fibers and a net of polymeric filaments and a second layer of a web of melt blown microfibers on a first aperturing member having aperturing means of a first size sufficient for forming apertures;
impinging streams of high pressure liquid onto the fiber layers for a time sufficient to entangle said fibers with one another such that the fibers interlock to form a fabric and to create apertures of a first size;
transferring said fabric to a second aperturing member having aperturing means of a second size sufficient for forming apertures; and
impinging streams of high pressure liquid onto the fabric for a time sufficient to form apertures of a second size in said fabric.

2. The process of claim 1, further comprising supporting a third layer of a web of textile fibers on said second layer on said first aperturing member prior to impinging streams of high pressure liquid onto the fiber webs.

3. The process of claim 1, wherein said supporting step is preceded by the additional steps of:
extruding a web of drawn continuous filament textile fibers onto a continuous belt;
extruding a web of melt blown microfibers onto said web of drawn continuous filament textile fibers on said continuous belt; and
transferring said webs to said first aperturing member.

4. The process of claim 3, further comprising extruding a second web of drawn continuous filament textile fibers onto said melt blown microfiber web prior to said transferring step.

5. The process of claim 1, wherein said supporting step is preceded by the additional steps of:
supplying a bonded web of drawn continuous filament textile fibers to a continuous belt;
extruding a web of melt blown microfibers onto said web of drawn continuous filament textile fibers on said continuous belt; and
transferring said webs to said first aperturing member.

6. The process of claim 5, further comprising supplying a second web of bonded drawn continuous filament textile fibers onto said melt blown microfiber web prior to said transferring step.

7. The process of claim 1, wherein said supporting step is preceded by the additional steps of:
supplying a bonded web of drawn continuous filament textile fibers to a continuous belt;
supplying a bonded web of melt blown microfibers onto said web of drawn continuous filament textile fibers on said continuous belt; and
transferring said web to said first aperturing member.

8. The process of claim 7, further comprising supplying a second bonded web of drawn continuous filament textile fibers onto said melt blown microfiber web prior to said transferring step.

9. The process of claim 1, wherein said supporting step is preceded by the additional steps of:
carding a web of staple textile fibers onto a continuous belt;
extruding a web of melt blown microfibers onto said web of carded staple textile fibers on said continuous belt; and
transferring said webs to said first aperturing member.

10. The process of claim 9, further comprising carding a second web of staple textile fibers onto said melt blown microfiber web prior to said transferring step.

11. The process of claim 1, wherein said supporting step is preceded by the additional steps of:
carding a web of staple textile fibers onto a continuous belt;
supplying a bonded web of melt blown microfibers onto said web of carded staple textile fibers on said continuous belt; and transferring said webs to said first aperturing member.

12. The process of claim 11, further comprising carding a second web of staple textile fibers onto said melt blown microfiber web prior to said transferring step.

13. The process of claim 1, wherein said supporting step is preceded by the additional steps of:
supplying a bonded web of carded staple textile fibers onto a continuous belt;
supplying a bonded web of melt blown microfibers onto said bonded web of carded staple textile fibers on said continuous belt; and
transferring said webs to said first aperturing member.

14. The process of claim 13, further comprising supplying a second bonded carded web of staple textile fibers onto said melt blown microfiber web prior to said transferring step.

15. The process of claim 1, wherein said supporting step is preceded by the additional steps of:
supplying a bonded web of carded staple textile fibers onto a continuous belt;
extruding a web of melt blown microfibers onto said web of bonded cable staple textile fibers on said continuous belt; and
transferring said webs to said first aperturing member.

16. The process of claim 15, further comprising supplying a second bonded web of carded staple textile fibers onto said melt blown microfiber web prior to said transferring step.

17. The process of claim 1, wherein said supporting step is preceded by the additional steps of:
extruding a web of melt blown microfibers onto a continuous belt;
carding a web of staple textile fibers onto said web of melt blown microfibers on said continuous belt; and
transferring said webs to said first aperturing member.

18. The process of claim 1, wherein said supporting step is preceded by the additional steps of:
supplying a bonded web of melt blown microfibers onto a continuous belt;
carding a web of staple textile fibers onto said web of melt blown microfibers on said continuous belt; and
transferring said webs to said first aperturing member.

19. The process of claim 1, wherein said supporting step is preceded by the additional steps of:
extruding a web of melt blown microfibers onto a continuous belt;
supplying a bonded web of carded staple textile fibers onto said web of melt blown microfibers on said continuous belt; and
transferring said webs to said first aperturing member.

20. The process of claim 1, wherein said supporting step is preceded by the additional steps of:
supplying a bonded web of melt blown microfibers onto a continuous belt;
supplying a bonded web of carded staple textile fibers onto said web of melt blown microfibers on said continuous belt; and
transferring said webs to said first aperturing member 21. The process of claim 1, wherein said supporting step is preceded by the additional steps of:
extruding a web of drawn continuous filament textile fibers onto a continuous belt;
supplying a bonded web of melt blown microfibers onto said web of drawn continuous filament textile fibers; and
transferring said webs to said first aperturing member.

22. The process of claim 1, wherein said supporting step is preceded by the additional steps of:
supplying a net of polymeric filaments onto a continuous belt;
extruding a web of meltblown microfibers onto the net on the continuous belt; and
transferring said net and web to said first aperturing member.

23. The process of claim 1, wherein said supporting step is preceded by the additional steps of:
supplying a net of polymeric filaments onto a continuous belt;
supplying a bonded web of melt blown microfibers onto the net of the continuous belt; and
transferring said net and web to said first aperturing member.

24. A process for producing a nonwoven fabric comprising:
supporting a net of polymeric filaments and a web of melt blown microfibers on an aperturing member; and
impinging streams of high pressure liquid onto the webs for a time sufficient to entangle the webs with one another such that the webs interlock to form a fabric.

25. The process of claim 24, further comprising before said supporting step, the steps of:
supplying said net of polymeric filaments onto a continuous belt;
extruding said web of melt blown microfibers onto the net on the continuous belt; and
transferring said net and said web to said aperturing member.

26. The process of claim 25, further comprising before said supporting step, the steps of:
supplying said net of polymeric filaments onto a continuous belt;
supplying a bonded web of melt blown microfibers onto the net on the continuous belt; and
transferring said net and said web to said aperturing member.

* * * * *

UNITED STATES PATENT AND TRADEMARK OFFICE
CERTIFICATE OF CORRECTION

PATENT NO. : 5,369,858

DATED : December 6, 1994

INVENTOR(S) : Thomas Gilmore et al.

It is certified that error appears in the above-identified patent and that said Letters Patent is hereby corrected as shown below:

On title page, item [56] page 2, the reference listed as:

" "Progress with Sontara and Spunlaced Fabrics in Europe", Nonwovens Report, Jan. 1987, pp. 7-8 "

should be:

-- "Progress with Sontara and Spunlaced Fabrics in Europe", Nonwoven Report, Jan. 1978, pp. 7-8" --.

Column 1, line 39, "hydrophic" should be -- hydrophilic --.

Column 4, line 11, "cf" should be -- of --.

Column 4, line 19, after "the" (first occurrence) delete the comma -- , --.

Column 4, line 49, "6 A" should be -- 6A --.

Column 5, lines 60-61, "Peterson" should be -- Petersen --.

Column 6, line 23, after "However" the period "." should be a comma -- , --.

Column 6, line 24, "cf" should be -- of --.

Column 7, line 40, "wed" should be -- web --.

UNITED STATES PATENT AND TRADEMARK OFFICE
CERTIFICATE OF CORRECTION

PATENT NO. : 5,369,858

DATED : December 6, 1994

INVENTOR(S) : Thomas Gilmore et al.

It is certified that error appears in the above-identified patent and that said Letters Patent is hereby corrected as shown below:

Column 8, line 18, "*Nonwovens Industry*" should be
-- *Nonwovens Technology* --.

Column 8, line 51, after "onto-a" should be -- onto a --.

Column 9, line 21, "Jet" should be -- jet --.

Column 9, line 26, "spaces" should be -- spaced --.

Column 9, line 48, "*Nonwoven's Industry*" should be
-- *Nonwovens Technology* --.

Column 12, line 3, after "web" insert a period -- . --.

Column 12, line 56, after "drum" insert -- 34' --.

Column 12, line 60, "Jet" should be -- jet --.

Column 13, line 15, "step" (second occurrence) should be
-- the --.

Column 13, line 59, " 2140" " should be -- 21''' --.

Column 16, line 57, "condition" should be
-- conditions --.

Column 17, line 41, "Begbin-Say" should be
-- Beghin-Say --.

Column 17, lines 45-46, after "10 g/yd$^2$" insert a
period -- . --.

UNITED STATES PATENT AND TRADEMARK OFFICE
CERTIFICATE OF CORRECTION

PATENT NO. : 5,369,858

DATED : December 6, 1994

INVENTOR(S) : Thomas Gilmore et al.

It is certified that error appears in the above-identified patent and that said Letters Patent is hereby corrected as shown below:

Column 18, line 15, "(SEMI" should be -- (SEM) --.

Column 19, line 18, "D168264" should be -- D1682-64 --.

Columns 19-20, in Table 1, each occurrence of "CEREX$^R$" should be -- CEREX® --.

Columns 21-22, in Table 1, each occurrence of "CEREX$^R$" should be -- CEREX® --.

Column 24, line 45, "web" should be -- webs --.

Column 25, line 24, "cable" should be -- carded --.

Column 25, line 28, "claim 15" should be -- claim 14 --.

Column 26, line 8, after "member" insert a period -- . --.

Signed and Sealed this

Twenty-fifth Day of April, 1995

Attest:

BRUCE LEHMAN

Attesting Officer

Commissioner of Patents and Trademarks